US010799728B2

(12) United States Patent
Gordon

(10) Patent No.: US 10,799,728 B2
(45) Date of Patent: Oct. 13, 2020

(54) RESPIRATORS AND RELATED METHODS

(71) Applicant: AIR 99 LLC, Boulder, CO (US)

(72) Inventor: Richard Gordon, Boulder, CO (US)

(73) Assignee: AIR99 LLC, Boulder, CO (US)

( * ) Notice: Subject to any disclaimer, the term of this patent is extended or adjusted under 35 U.S.C. 154(b) by 272 days.

(21) Appl. No.: 15/443,643

(22) Filed: Feb. 27, 2017

(65) Prior Publication Data

US 2018/0243592 A1 Aug. 30, 2018

(51) Int. Cl.

| | |
|---|---|
| ***A61B 18/08*** | (2006.01) |
| ***A62B 18/08*** | (2006.01) |
| ***A62B 23/02*** | (2006.01) |
| *A62B 18/02* | (2006.01) |

(52) U.S. Cl.
CPC .......... *A62B 18/084* (2013.01); *A62B 23/025* (2013.01); *A62B 18/025* (2013.01)

(58) Field of Classification Search
CPC .... A62B 18/025; A62B 18/084; A62B 23/025
See application file for complete search history.

(56) References Cited

U.S. PATENT DOCUMENTS

| | | | |
|---|---|---|---|
| 2,752,916 A | 7/1956 | Haliczer | |
| 4,248,220 A | 2/1981 | White | |
| 5,553,608 A | 9/1996 | Reese et al. | |
| 6,474,336 B1 | 11/2002 | Wolfe | |
| D638,171 S | 5/2011 | Goranov et al. | |
| 8,052,821 B2 | 11/2011 | Cheng | |
| 8,118,026 B2 | 2/2012 | Gebrewold et al. | |
| D658,334 S | 4/2012 | Goranov et al. | |
| 8,439,038 B2 | 5/2013 | Steindorf et al. | |
| 8,967,147 B2 * | 3/2015 | Martin | A62B 18/025 128/206.19 |
| 2005/0096524 A1 | 5/2005 | Cheng | |
| 2006/0130841 A1 | 6/2006 | Spence et al. | |

(Continued)

FOREIGN PATENT DOCUMENTS

| | | |
|---|---|---|
| WO | 2001089330 A2 | 11/2001 |
| WO | 2014199378 | 12/2014 |

OTHER PUBLICATIONS

The International Search Report and Written Opinion for corresponding Int'l Application No. PCT/US18/19937 dated Jun. 29, 2018.

*Primary Examiner* — Amber R Stiles
(74) *Attorney, Agent, or Firm* — Bryan Cave Leighton Paisner LLP

(57) ABSTRACT

Some embodiments include a respirator. The respirator includes a mask structure comprising one or more layers, multiple folds, and a contact surface region, and the one or more layers include a filtration layer. Meanwhile, the respirator includes an attachment mechanism coupled to the mask structure. The attachment mechanism is operable to couple the mask structure to a face region of a user. The user has a maxilla bone having a first frontal process and a second frontal process, and when the mask structure is coupled to the face region of the user by the attachment mechanism, the multiple folds conform the contact surface region to the face region of the user over the first frontal process of the maxilla bone and over the second frontal process of the maxilla bone. Other embodiments of related respirators and methods are also disclosed.

20 Claims, 10 Drawing Sheets

(56) References Cited

U.S. PATENT DOCUMENTS

| | | | |
|---|---|---|---|
| 2006/0201513 | A1 | 9/2006 | Chu |
| 2009/0078264 | A1 | 3/2009 | Martin et al. |
| 2009/0320848 | A1* | 12/2009 | Steindorf et al. .... A62B 23/025 |
| 2011/0094515 | A1* | 4/2011 | Duffy ................. A41D 13/1138 128/206.19 |
| 2015/0305417 | A1 | 10/2015 | Martin |

* cited by examiner

RESPIRATORS AND RELATED METHODS

FIELD OF THE INVENTION

This invention relates generally to respirators, and relates more particularly to face-piece respirators having multiple folds and/or one or more constraining mechanisms and methods of providing the same.

DESCRIPTION OF THE BACKGROUND

Numerous studies have correlated air pollution to higher probabilities of heart and lung disease, higher mortality, and lower quality of life. Further, airborne particles smaller than approximately 10 micrometers in diameter pose a significant health risk to humans. When inhaled, such airborne particles can lodge deep within human lungs where the particles cause an increased probability of contracting lung and heart disease. Infants and children whose lungs are still developing, and the elderly with reduced lung capacity, are at even greater health risk from exposure to polluted air than average adults.

A face-piece respirator can filter the air a user breathes to prevent or limit the user from inhaling airborne contaminants, airborne pathogens, gases, aerosols, etc. A respirator efficiency of the face-piece respirator is a measure of a particle count of one or more types of substances (e.g., one or more restricted substance(s), as defined below) in a volume of air located inside the face-piece respirator when the face-piece respirator is being used relative to a particle count of the one or more types of substances in a same volume of air located just outside of the face-piece respirator.

Airborne contaminants, airborne pathogens, gases, aerosols, etc. are more likely to be inhaled by a user when a face-piece respirator is poorly fitted as a result of air leaks formed along a periphery of the face-piece respirator. Air leakage along the periphery of a face-piece respirator translates into a lower air-filtration efficiency. The higher an air-filtration efficiency of a face-piece respirator is, the cleaner the air inside the mask is to breathe.

Accordingly, a need or potential for benefit exists for face-piece respirators having improved fit and air-filtration efficiency.

BRIEF DESCRIPTION OF THE DRAWINGS

To facilitate further description of the embodiments, the following drawings are provided in which.

Figure 1:
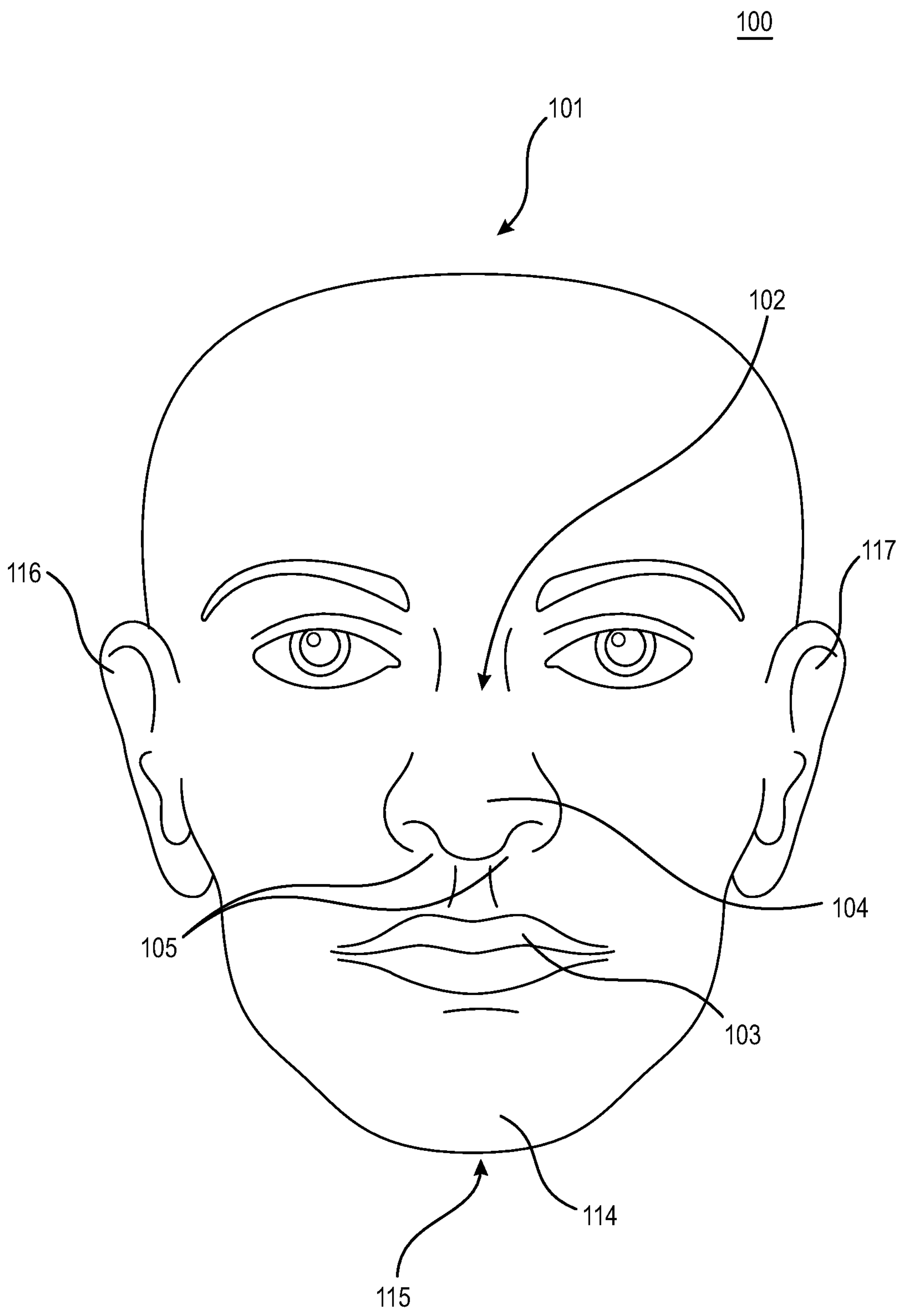
FIG. 1 illustrates a head of an exemplary human.

For simplicity and clarity of illustration, the drawing figures illustrate the general manner of construction, and descriptions and details of well-known features and techniques may be omitted to avoid unnecessarily obscuring the invention. Additionally, elements in the drawing figures are not necessarily drawn to scale. For example, the dimensions of some of the elements in the figures may be exaggerated relative to other elements to help improve understanding of embodiments of the present invention. The same reference numerals in different figures denote the same elements.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Furthermore, the terms "include," and "have," and any variations thereof, are intended to cover a non-exclusive inclusion, such that a process, method, system, article, device, or apparatus that comprises a list of elements is not necessarily limited to those elements, but may include other elements not expressly listed or inherent to such process, method, system, article, device, or apparatus.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments of the invention described herein are, for example, capable of operation in other orientations than those illustrated or otherwise described herein.

The terms "couple," "coupled," "couples," "coupling," and the like should be broadly understood and refer to connecting two or more elements or signals, electrically, mechanically and/or otherwise. Two or more electrical elements may be electrically coupled but not be mechanically or otherwise coupled; two or more mechanical elements may be mechanically coupled, but not be electrically or otherwise coupled; two or more electrical elements may be mechanically coupled, but not be electrically or otherwise coupled. Coupling may be for any length of time, e.g., permanent or semi-permanent or only for an instant.

"Electrical coupling" and the like should be broadly understood and include coupling involving any electrical signal, whether a power signal, a data signal, and/or other types or combinations of electrical signals. "Mechanical coupling" and the like should be broadly understood and include mechanical coupling of all types.

The absence of the word "removably," "removable," and the like near the word "coupled," and the like does not mean that the coupling, etc. in question is or is not removable.

As defined herein, "approximately" can, in some embodiments, mean within plus or minus ten percent of the stated value. In other embodiments, "approximately" can mean within plus or minus five percent of the stated value. In further embodiments, "approximately" can mean within plus or minus three percent of the stated value. In yet other embodiments, "approximately" can mean within plus or minus one percent of the stated value.

DETAILED DESCRIPTION OF EXAMPLES OF EMBODIMENTS

Some embodiments include a respirator. The respirator comprises a mask structure comprising one or more layers, multiple folds, and a contact surface region, and the one or more layers comprise a filtration layer. Meanwhile, the respirator comprises an attachment mechanism coupled to the mask structure. The attachment mechanism can be operable to couple the mask structure to a face region of a user. The user has a maxilla bone having a first frontal process and a second frontal process, and when the mask structure is coupled to the face region of the user by the attachment mechanism, the multiple folds can conform the contact surface region to the face region of the user over the first frontal process of the maxilla bone and over the second frontal process of the maxilla bone.

Further embodiments include a respirator. The respirator comprises a mask structure, and the mask structure comprises one or more layers, multiple folds, a left side, and a right side opposite the left side. The one or more layers comprise a filtration layer. Further, the respirator comprises an attachment mechanism coupled to the mask structure. The attachment mechanism can be operable to couple the mask structure to a face region of a user. Further still, the respirator comprises a first constraining mechanism and a second constraining mechanism. Meanwhile, the mask structure can be constrained together proximal to the left side by the first constraining mechanism, the mask structure can be constrained together proximal to the right side by the second constraining mechanism, and the multiple folds can be arranged such that the mask structure fans out toward the right side proximal to where the mask structure is constrained by the first constraining mechanism and the mask structure fans out toward the left side proximal to where the mask structure is constrained by the second constraining mechanism.

Further embodiments include a respirator. The respirator comprises a mask structure comprising one or more layers and multiple folds. The one or more layers comprise a filtration layer. Meanwhile, the respirator comprises an attachment mechanism coupled to the mask structure. The attachment mechanism can be operable to couple the mask structure to a face region of a user. Further, the multiple folds can comprise plural folds arranged to cause at least part of the mask structure to behave auxetically.

Figure 2:
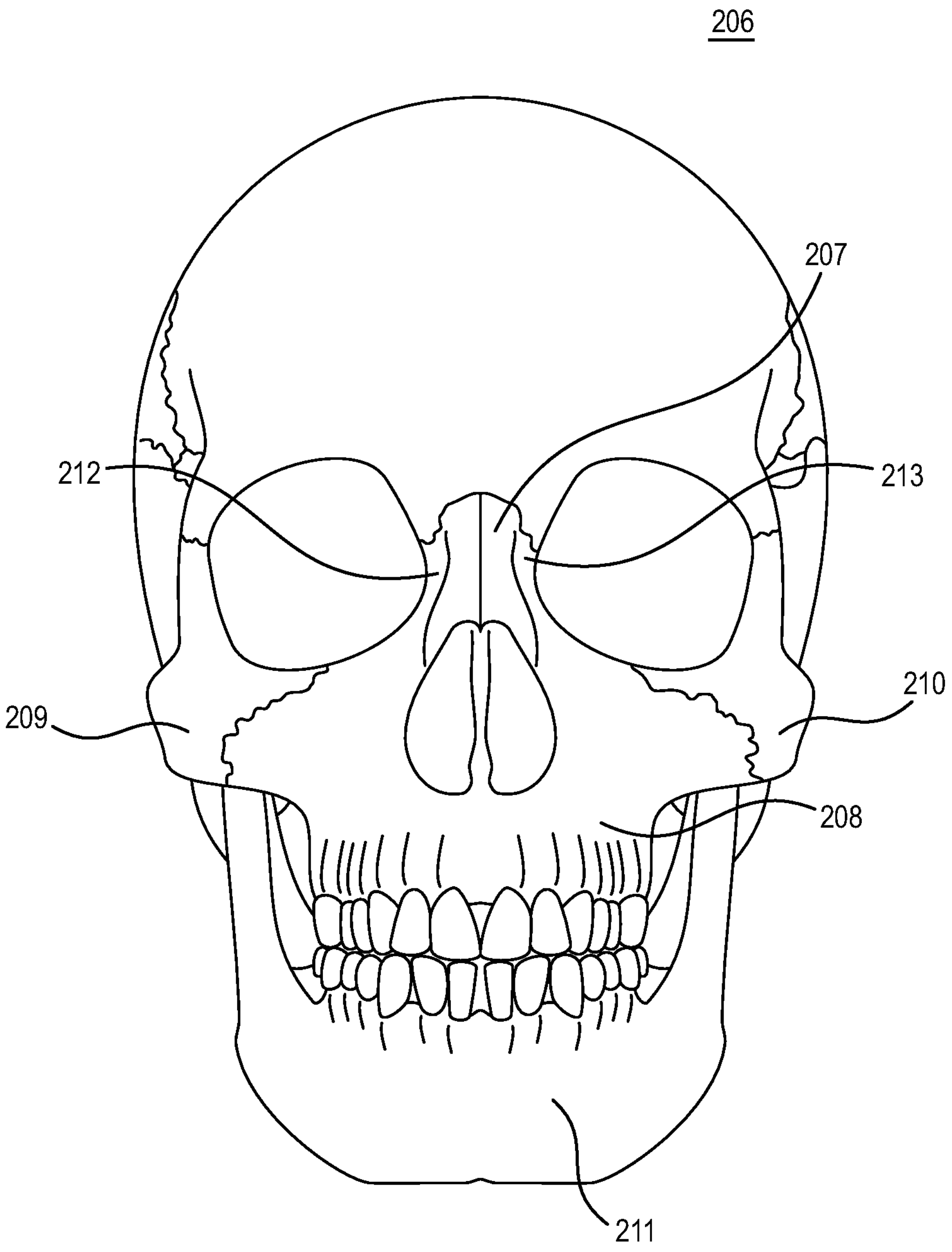
FIG. 2 illustrates a skull of the head of FIG. 1.

Turning to the drawings, FIGS. 1 & 2 illustrate various human anatomical features providing context for various embodiments described herein. More specifically, FIG. 1 illustrates head 101 of an exemplary human 100, and FIG. 2 illustrates skull 206 of head 101 (FIG. 1). Referring first to FIG. 1, head 101 includes face region 102, submental region 115, right ear 116, and left ear 117. Further, face region 102 includes mouth 103, nose 104, which includes nostrils 105, and chin 114. Meanwhile, referring to FIG. 2, skull 206 includes nasal bone 207, maxilla bone 208, right zygomatic bone 209, left zygomatic bone 210, and mandible bone 211, all of which underlie face region 102 (FIG. 1). Further, maxilla bone 208 includes right frontal process 212 and left frontal process 213.

Figure 3:
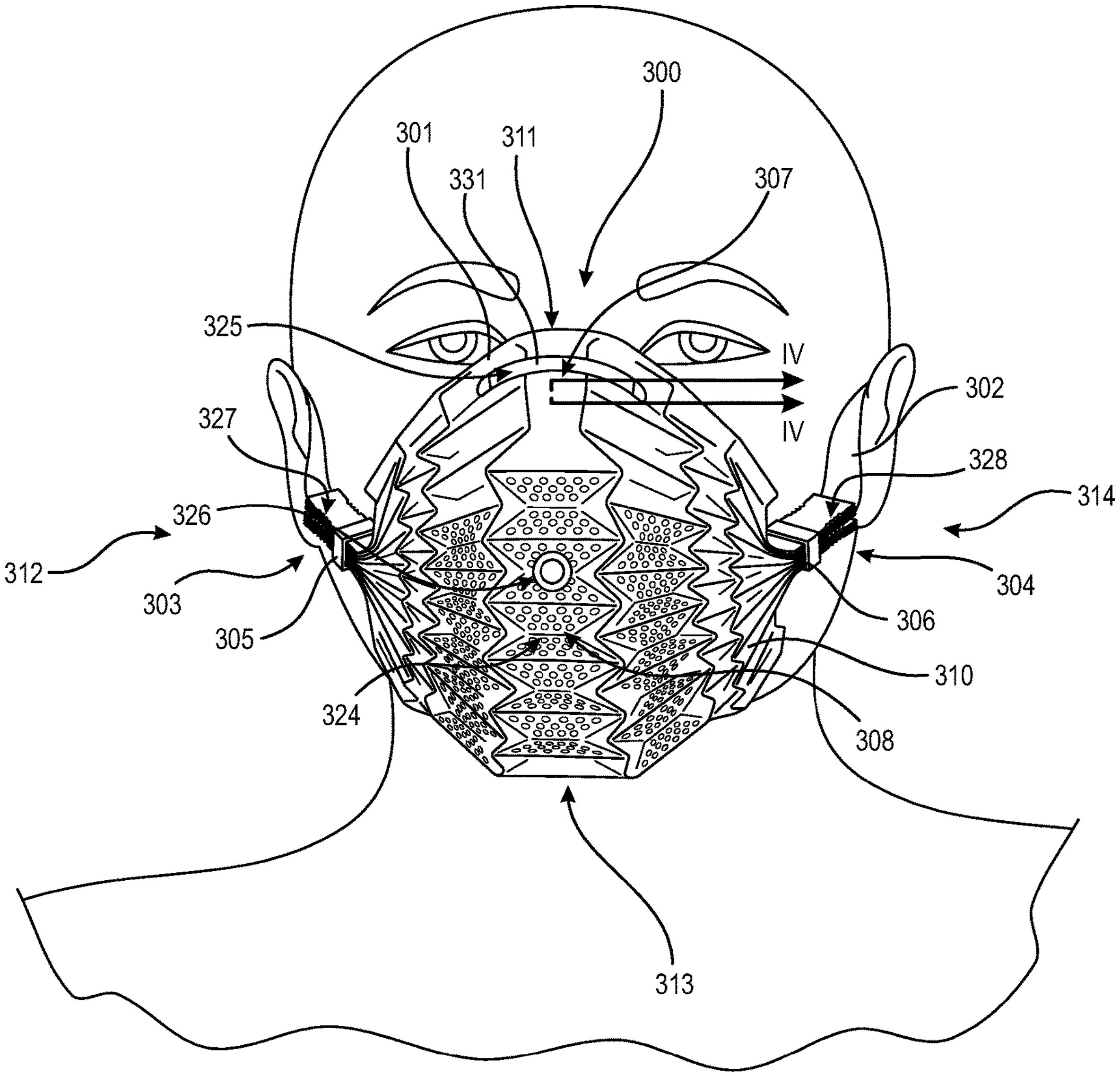
FIG. 3 illustrates a front view of a respirator, according to an embodiment.

Turning ahead in the drawings, FIG. 3 illustrates a front view of respirator 300, according to an embodiment. Respirator 300 is merely exemplary and is not limited to the embodiments presented herein. Respirator 300 can be employed in many different embodiments or examples not specifically depicted or described herein.

As discussed in greater detail below, in many embodiments, respirator 300 can be operable as a face-piece respirator. For example, respirator 300 can be operable to prevent or limit a user and/or one or more other persons from inhaling one or more restricted substances. In many embodiments, the user and/or other person(s) can be similar or identical to human 100 (FIG. 1). Meanwhile, as used herein, restricted substance(s) can refer to (i) one or more substances that would be harmful to the user and/or the other person(s) if inhaled and/or (ii) one or more substances that the user and/or the other person(s) do not desire to inhale. Exemplary restricted substance(s) can include one or more airborne particles (e.g., one or more airborne particles having a largest dimension (e.g., diameter) of less than or equal to approximately 10 micrometers), one or more airborne pathogens, one or more gases (e.g., one or more vapors), one or more aerosols, etc. In more specific examples, restricted substance(s) can include one or more airborne substances originating from industrial or commercial processes, combustion (e.g., fossil fuel combustion), or meteorological phenomena (e.g., dust storms), one or more viral pathogens, one or more bacterial pathogens, etc. By filtering out airborne particles, respirator 300 also will filter out large particles.

Respirator 300 comprises mask structure 301 and attachment mechanism 302. Further, respirator 300 can comprise right constraining mechanism 303, left constraining mechanism 304, right adjustment mechanism 305 and/or left adjustment mechanism 306. As discussed in greater detail below, in some embodiments, attachment mechanism 302 can comprise right constraining mechanism 303 and/or left constraining mechanism 304; right constraining mechanism 303 can comprise right adjustment mechanism 305; left constraining mechanism 304 can comprise left adjustment mechanism 306; right constraining mechanism 303 can comprise left constraining mechanism 304, and vice versa; and/or right adjustment mechanism 305 can comprise left adjustment mechanism 306, and vice versa. Meanwhile, in these or other embodiments, one or more of right constraining mechanism 303, left constraining mechanism 304, right adjustment mechanism 305 and left adjustment mechanism 306 can be omitted.

Figure 6:
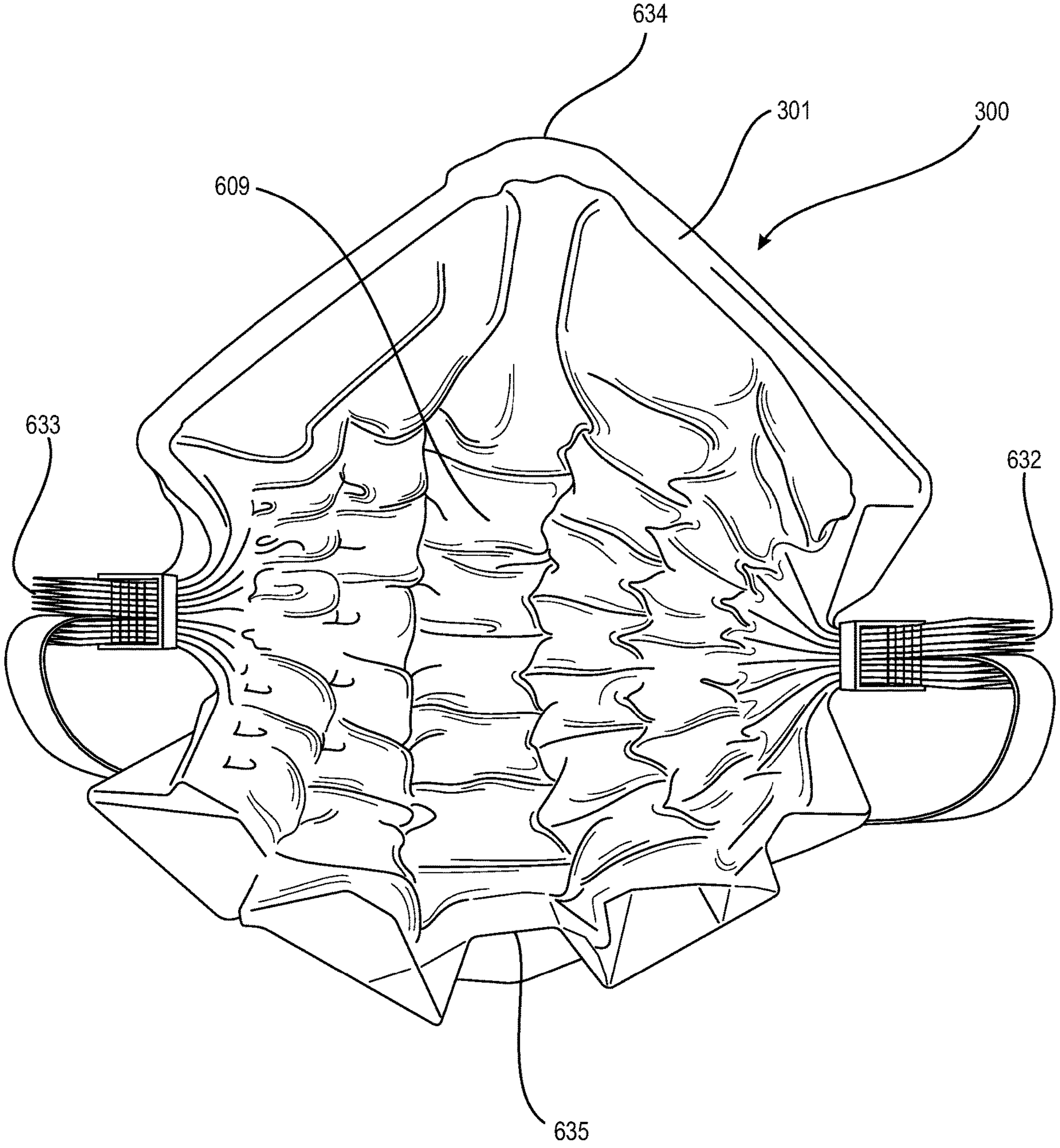
FIG. 6 illustrates a rear view of the respirator, according to the embodiment of FIG. 3.

In many embodiments, mask structure 301 can comprise one or more layers 307, multiple folds 308, contact surface 609 (FIG. 6), and exterior surface 310. Mask structure 301 can comprise right edge 632 (FIG. 6), left edge 633 (FIG. 6), top edge 634 (FIG. 6), and bottom edge 635 (FIG. 6). In some embodiments, mask structure 301 can comprise one or more respiration apertures 324, one or more malleable bands 325, one or more exhalation valves 326, one or more right adjustment mechanism stops 327, and/or one or more left adjustment mechanism stops 328. Further, malleable band(s) 325 can comprise nose malleable band 331. However, as discussed in greater detail below, in other embodiments, respiration aperture(s) 324, malleable band(s) 325, exhalation valve(s) 326, right adjustment mechanism stop(s) 327, and/or left adjustment mechanism stop(s) 328 can be omitted. Meanwhile, for reference purposes, mask structure 301 can comprise top side 311, right side 312, bottom side 313, and left side 314. Top side 311 can be opposite bottom side 313, and vice versa; and right side 312 can be opposite left side 314, and vice versa.

Figure 4:
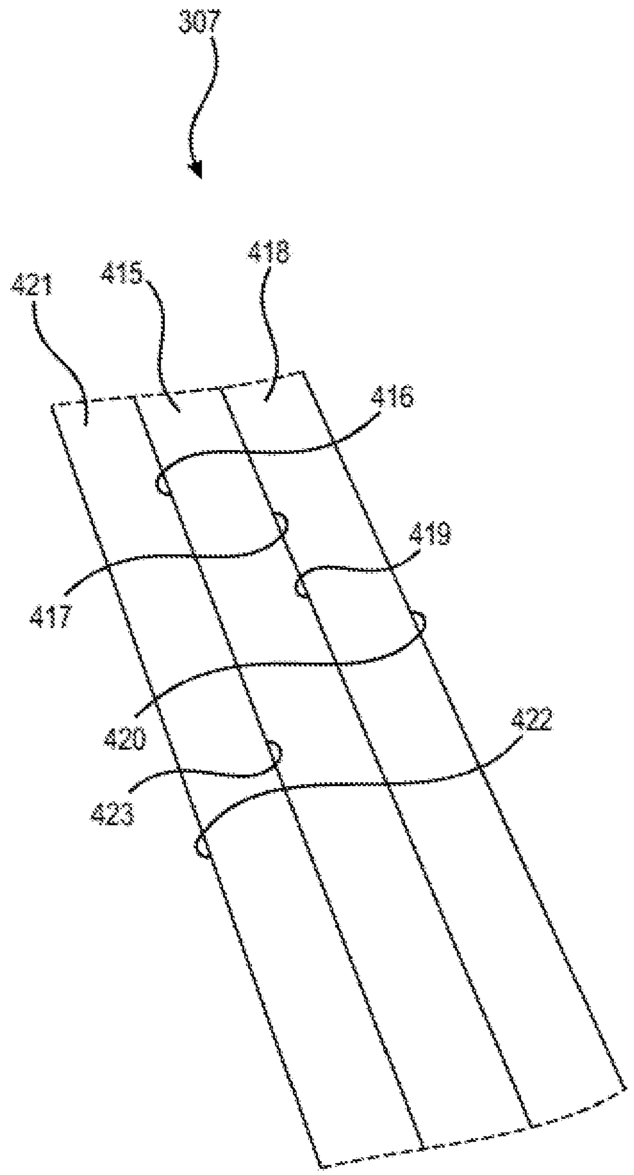
FIG. 4 illustrates an enlarged right side cross-sectional view of a mask structure of the respirator taken at lines IV-IV, according to the embodiment of FIG. 3.

Turning ahead in the drawings, FIG. 4 illustrates an enlarged right side cross-sectional view of mask structure 301 taken at lines IV-IV of FIG. 3, according to the embodiment of FIG. 3. Layer(s) 307 can comprise filtration layer 415, which can comprise filtration layer first surface 416 and filtration layer second surface 417 opposite filtration layer first surface 416. In some embodiments, layer(s) 307 can comprise support layer 418, which can comprise support layer first surface 419 and support layer second surface 420 opposite support layer first surface 419. In further embodiments, layer(s) 307 can comprise contact layer 421, which can comprise contact layer first surface 422 and contact layer second surface 423 opposite contact layer first surface 422. As discussed in greater detail below, in other embodiments, support layer 418 and/or contact layer 421 can be omitted.

In many embodiments, filtration layer 415 can be permeable to oxygen and impermeable to at least one or more restricted substances. That is, filtration layer 415 can function as a filter to the restricted substance(s). In further embodiments, filtration layer 415 also can be permeable to one or more other gases, such as, for example, nitrogen, argon, carbon dioxide, hydrogen, neon, krypton, helium, methane, etc. In these or other embodiments, filtration layer 415 can be permeable to air less the restricted substance(s).

In some embodiments, filtration layer 415 can operate as a filter having a filter rating as defined by the National Institute for Occupational Safety and Health of the United States of America. For example, the filter rating of filtration layer 415 can comprise one of an N95, N99, N100, P95, or P99 filter rating. In many embodiments, the filter rating implemented for filtration layer 415 can be selected in accordance with the restricted substance(s) that filtration layer 415 is intended to filter out. In some embodiments, filtration layer 415 can comprise a filter paper manufactured by Hollingsworth & Vose Company of East Warpole, Mass., United States of America.

Further, filtration layer 415 can comprise one or more filtration layer materials. The filtration layer material(s) can comprise any suitable material or materials that are permeable to oxygen or air and impermeable to the restricted substance(s). For example, the filtration layer material(s) can comprise polypropylene and/or polyester.

Further, filtration layer 415 can comprise a filtration layer thickness extending between filtration layer first surface 416 and filtration layer second surface 417. In many embodiments, the filtration layer thickness of filtration layer 415 can be greater than or equal to approximately 0.2794 millimeters and/or less than or equal to approximately 1.7526 millimeters. However, generally, the filtration layer thickness of filtration layer 415 can be any suitable thickness permitting filtration layer 415 to function as a filter to the restricted substance(s) and to permit multiple folds 308 (FIG. 3) to be formed in mask structure 301 (FIG. 3). For example, in some embodiments, the filtration layer thickness of filtration layer 415 can be approximately 0.508 millimeters.

Further, filtration layer 415 can comprise a filtration layer grammage or basis weight. For example, the filtration layer grammage can be greater than or equal to approximately 50 grams per square meter and/or less than or equal to approximately 178 grams per square meter. However, generally, the filtration layer grammage of filtration layer 415 can be any suitable grammage permitting filtration layer 415 to function as a filter to the restricted substance(s) and to permit multiple folds 308 (FIG. 3) to be formed in mask structure 301 (FIG. 3). For example, in some embodiments, the filtration layer grammage of filtration layer 415 can be approximately 70 grams per square meter.

Further, filtration layer 415 can comprise an air flow resistance. For example, in some embodiments, the air flow resistance of filtration layer 415 can be greater than or equal to approximately 8.6 millimeters of water when tested with an automated filter tester model 8130 of TSI Incorporated of Shoreview, Minn., United States of America for an air flow rate of 85 liters per minute over a filtered area of 170 square centimeters. In these or other embodiments, the air flow resistance of filtration layer 415 can be less than or equal to approximately 20 millimeters of water when tested with an automated filter tester model 8130 of TSI Incorporated of Shoreview, Minn., United States of America for an air flow rate of 85 liters per minute over a filtered area of 170 square centimeters. In many embodiments, the air flow resistance of filtration layer 415 can be approximately 13.7 millimeters of water when tested with an automated filter tester model 8130 of TSI Incorporated of Shoreview, Minn., United States of America for an air flow rate of 85 liters per minute over a filtered area of 170 square centimeters.

Further, filtration layer 415 can comprise filtration efficiency. For example, in many embodiments, the filtration efficiency of filtration layer 415 can be greater than or equal to approximately 95% or 99% for 2.5 micron-sized test particles. In these embodiments, the test particles can include petroleum-based aerosols or be devoid of petroleum-based aerosols. In other embodiments, the filtration efficiency of filtration layer 415 can be approximately 100% for 2.5 micron-sized test particles. In these embodiments, the test particles can be devoid of petroleum-based aerosols.

In many embodiments, support layer 418 can function to support mask structure 301 (FIG. 3) to continuously maintain multiple folds 308 (FIG. 3) in mask structure 301 (FIG. 3) after multiple folds 308 (FIG. 3) are formed in mask structure 301 (FIG. 3). In these or other embodiments, support layer 418 also can function to protect filtration layer 415. In some embodiments, support layer 418 can comprise a paper manufactured by the Yupo Corporation America of Chesapeake, Va., United States of America. In some embodiments, support layer 418 can be impermeable to water, air, and/or oxygen.

Further, support layer 418 can comprise one or more support layer materials. The support layer material(s) can comprise any suitable material or materials that are able to support mask structure 301 (FIG. 1) to continuously maintain multiple folds 308 (FIG. 3) in support layer 418 after multiple folds 308 (FIG. 3) are formed in mask structure 301 (FIG. 3). For example, the support layer material(s) can comprise polypropylene and/or polyester.

Further, support layer 418 can comprise a support layer thickness extending between support layer first surface 419 and support layer second surface 420. In many embodiments, the support layer thickness of support layer 418 can be greater than or equal to approximately 0.11 millimeters and/or less than or equal to approximately 0.17 millimeters. However, generally, the support layer thickness of support layer 418 can be any suitable thickness permitting multiple folds 308 (FIG. 3) to be formed in mask structure 301 (FIG. 3) and support layer 418 to support mask structure 301 (FIG. 3) to continuously maintain multiple folds 308 (FIG. 3) in support layer 418 after multiple folds 308 (FIG. 3) are formed in mask structure 301 (FIG. 3).

Further, support layer 418 can comprise a support layer grammage or basis weight. For example, the support layer grammage can be greater than or equal to approximately 15 grams per square meter and/or less than or equal to approximately 30 grams per square meter. However, generally, the support layer grammage of support layer 418 can be any suitable grammage permitting multiple folds 308 (FIG. 3) to be formed in mask structure 301 (FIG. 3) and support layer 418 to support mask structure 301 (FIG. 3) to continuously maintain multiple folds 308 (FIG. 3) in support layer 418 after multiple folds 308 (FIG. 3) are formed in mask structure 301 (FIG. 3).

In many embodiments, contact layer 421 can function to provide capillary action to wick away moisture at contact layer first surface 422 and/or contact layer second surface 423. In these or other embodiments, contact layer 421 also can function to protect filtration layer 415. In some embodiments, contact layer 421 can comprise a paper manufactured by the Ahlstrom Corporation of Helsinki, Finland. In many embodiments, contact layer 421 can be permeable to oxygen or air.

Further, contact layer 421 can comprise one or more contact layer materials. The contact layer material(s) can comprise any suitable material or materials that are able to provide capillary action to wick away moisture at contact layer first surface 422 and/or contact layer second surface 423. For example, the contact layer material(s) can comprise polypropylene and/or polyester.

Further, contact layer 421 can comprise a contact layer thickness extending between contact layer first surface 422 and filtration layer second surface 423. In many embodiments, the contact layer thickness of contact layer 421 can be greater than or equal to approximately 0.07 millimeters and/or less than or equal to approximately 0.37 millimeters. However, generally, the contact layer thickness of contact layer 421 can be any suitable thickness permitting contact layer 421 to provide capillary action to wick away moisture at contact layer first surface 422 and/or contact layer second surface 423 and to permit multiple folds 308 (FIG. 3) to be formed in mask structure 301 (FIG. 3).

Further, contact layer 421 can comprise a contact layer grammage or basis weight. The contact layer grammage can be greater than or equal to approximately 15 grams per square meter and/or less than or equal to approximately 30 grams per square meter. However, generally in some embodiments, the contact layer grammage of contact layer 421 can be any suitable grammage permitting multiple folds 308 (FIG. 3) to be formed in mask structure 301 (FIG. 3) and contact layer 421 to support mask structure 301 (FIG. 3) to continuously maintain multiple folds 308 (FIG. 3) in contact layer 421 after multiple folds 308 (FIG. 3) are formed in mask structure 301 (FIG. 3).

In many embodiments, when layer(s) 307 comprise multiple layers (e.g., filtration layer 415 and support layer 418 and/or contact layer 421), layer(s) 307 can be arranged in a stack. For example, as shown at FIG. 4, when contact layer 421 is implemented, filtration layer 415 can be located over contact layer 421, and/or when support layer 418 is implemented, support layer 418 can be located over filtration layer 415. In these embodiments, locating contact layer 421 under filtration layer 415 can permit contact layer 421 to protect filtration layer 415; and/or locating support layer 418 over filtration layer 415 can permit support layer 418 to protect filtration layer 415.

In these or other embodiments, when layer(s) 307 comprise multiple layers (e.g., filtration layer 415 and support layer 418 and/or contact layer 421), adjacent pairs of layer(s) 307 can be coupled together. For example, when contact layer 421 is implemented, filtration layer first surface 416 can be coupled to contact layer second surface 423, and/or when support layer 418 is implemented, filtration layer second surface 417 can be coupled to support layer first surface 419. In these embodiments, adjacent pairs of layer(s) 307 can be coupled together in any suitable manner, including ultrasonic bonding, sewing, taping, adhering, etc. In some embodiments, adjacent pairs of layer(s) 307 can be coupled together along part or all of their perimeters and/or at part or all of multiple folds 308 (FIG. 3). In many embodiments, adjacent pairs of layer(s) 307 can be coupled together along all of their perimeters in order to form hermetic seals between the adjacent pairs of layer(s) 307 at the perimeters of the adjacent pairs of layer(s) 307.

In many embodiments, support layer 418 can be implemented when filtration layer 415 is unable to support mask structure 301 (FIG. 3) to continuously maintain multiple folds 308 (FIG. 3) in mask structure 301 (FIG. 3) after multiple folds 308 (FIG. 3) are formed in mask structure 301 (FIG. 3). In these or other embodiments, contact layer 421 can be implemented when filtration layer 415 is unable to provide capillary action to wick away moisture at filtration layer first surface 416 and/or filtration layer second surface 417. However, in some embodiments, filtration layer 415 can function (i) to support mask structure 301 (FIG. 3) to continuously maintain multiple folds 308 (FIG. 3) in mask structure 301 (FIG. 3) after multiple folds 308 (FIG. 3) are formed in mask structure 301 (FIG. 3) and/or (ii) to provide capillary action to wick away moisture at filtration layer first surface 416 and/or filtration layer second surface 417. Accordingly, when filtration layer 415 is able to support mask structure 301 (FIG. 3) to continuously maintain multiple folds 308 (FIG. 3) in mask structure 301 (FIG. 3) after multiple folds 308 (FIG. 3) are formed in mask structure 301 (FIG. 3), and in some embodiments, when filtration layer 415 is sufficiently robust to not tear during normal use, support layer 418 can be omitted. In these or other embodiments, when filtration layer 415 is able to provide capillary action to wick away moisture at filtration layer first surface 416 and/or filtration layer second surface 417, and in further embodiments, when filtration layer 415 is sufficiently robust to not tear during normal use, contact layer 421 can be omitted.

In some embodiments, contact surface 609 (FIG. 6) can comprise contact layer first surface 422, such as, for example, when contact layer 421 is implemented. In other embodiments, contact surface 609 (FIG. 6) can comprise filtration layer first surface 416, such as, for example, when contact layer 421 is omitted.

In these or other embodiments, exterior surface 310 (FIG. 3) can comprise support layer second surface 420, such as, for example, when support layer 418 is implemented. In other embodiments, exterior surface 310 (FIG. 3) can comprise filtration layer second surface 417, such as, for example, when support layer 418 is omitted.

Referring now back to FIG. 3, as indicated above, mask structure 301 can comprise multiple folds 308. In many embodiments, multiple folds 308 can comprise multiple mountain-valley folds. Further, multiple folds 308 can be arranged in one or more origami folding patterns.

In these or other embodiments, multiple folds 308 can comprise multiple horizontal folds, multiple vertical folds, and/or multiple diagonal folds. For example, in some embodiments, multiple folds 308 can comprise greater than or equal to approximately 7 horizontal folds and/or less than or equal to approximately 31 horizontal folds. In these or other embodiments, multiple folds 308 can comprise greater than or equal to approximately 3 vertical folds and/or less than or equal to approximately 12 vertical folds.

Applying a Cartesian coordinate system having an origin at a center point of mask structure 301 for purposes of reference, vertical folds can refer to folds extending from top side 311 to bottom side 313 approximately parallel to a y-axis of the Cartesian coordinate system, and horizontal folds can refer to folds extending from right side 312 to left side 314 approximately parallel to an x-axis of the Cartesian coordinate system. Also, vertical folds can be oriented approximately perpendicular to horizontal folds, and vice versa. Meanwhile, the Cartesian coordinate system can be oriented such that its x-axis approximately divides mask structure 301 into top and bottom halves and such that its y-axis approximately divides mask structure 301 into right and left halves. Further, when attachment mechanism 302 is coupling mask structure 301 to a face region of the user, as discussed below, the y-axis can be oriented approximately parallel with a length of a nose of the face region of the user. Additionally, diagonal folds can refer to folds having any other orientations than horizontal and vertical folds, and/or folds that skew with respect to the x-axis and the y-axis.

In many embodiments, multiple folds 308 can be formed in mask structure 301. For example, in some embodiments, multiple folds 308 can be folded into mask structure 301 in order to form multiple folds 308. In some embodiments, part or all of multiple folds 308 can be manually formed in mask structure 301 by hand. In further embodiments, part or all of multiple folds 308 can be automatically formed by one or more folding machines. In various embodiments, multiple folds 308 are formed in mask structure 301 other than by joining together (e.g., ultrasonically bonding together) the faces of multiple folds 308 at the fold lines of multiple folds 308.

In many embodiments, the locations where multiple folds 308 are formed in mask structure 301 can be determined using two-dimensional or three-dimensional parametric modeling. For example, in some embodiments, computer software can be programmed to implement two-dimensional or three-dimensional parametric modeling to generate a map of the fold lines corresponding to multiple folds 308 based on one or more parameter inputs. In some embodiments, the parameter inputs can comprise the number or numbers of horizontal, vertical, and/or diagonal folds, the distance or distances between the horizontal, vertical, and/or diagonal folds, the thickness or thicknesses of layer(s) 307, the diameter or diameters of any aperture(s) (as described below), etc. In further embodiments, the parameter inputs can be determined based on the anatomical dimensions of the user or of an average person.

Figure 5:
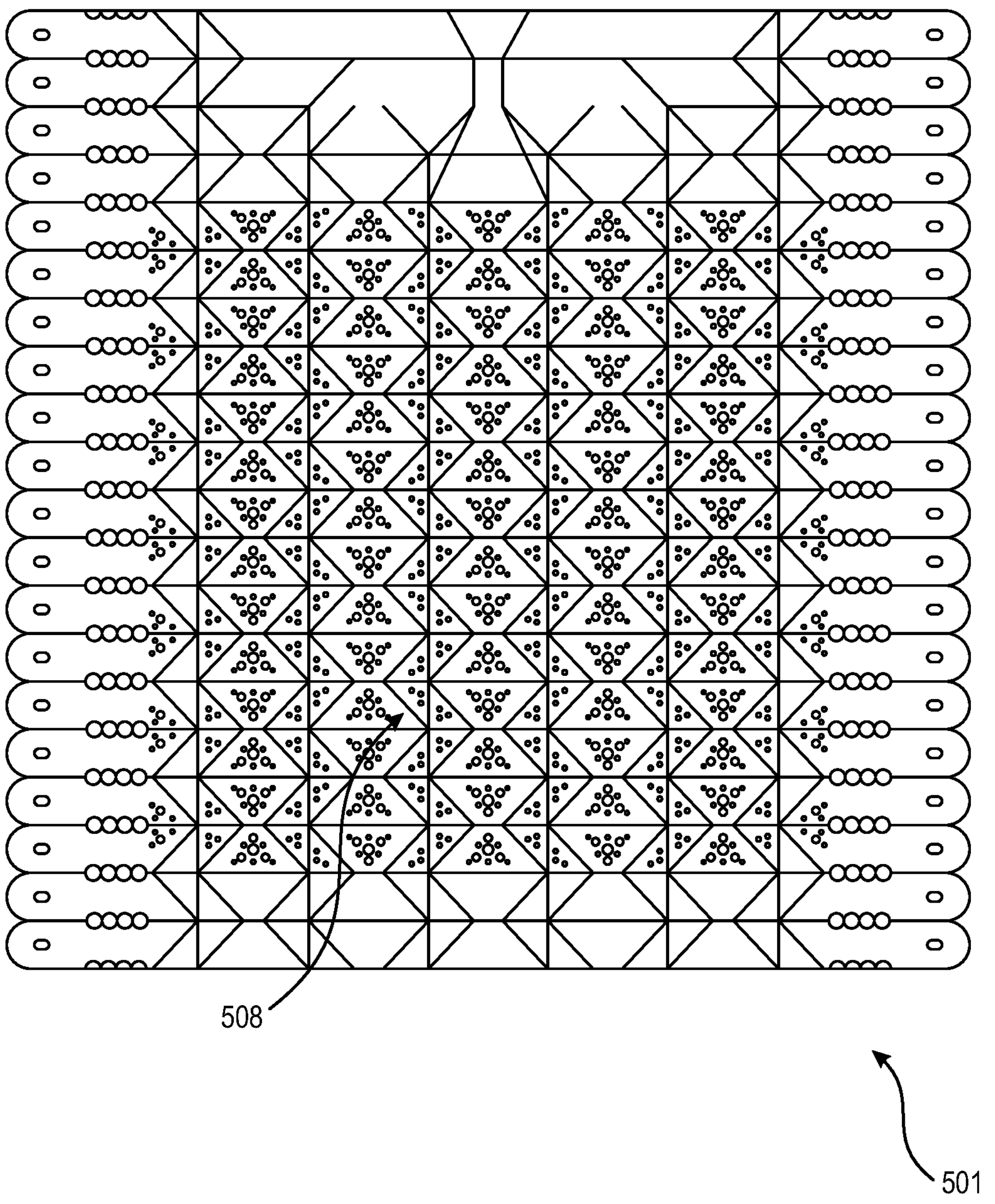
FIG. 5 illustrates an exemplary map of fold lines for multiple folds of a mask structure, according to an embodiment.

Turning ahead briefly in the drawings, FIG. 5 illustrates an exemplary map of fold lines for multiple folds 508 of mask structure 501, according to an embodiment. Mask structure 501 can be similar or identical to mask structure 301 (FIG. 3), and multiple folds 508 can be similar or identical to multiple folds 308 (FIG. 3).

Referring again to FIG. 3, in these or other embodiments, when layer(s) 307 comprise multiple layers (e.g., filtration layer 415 (FIG. 4) and support layer 418 (FIG. 4) and/or contact layer 421 (FIG. 4)), multiple folds 308 can be formed in mask structure 301 after adjacent pairs of layer(s) 307 are coupled together. In some embodiments, before multiple folds 308 are formed in mask structure 301, one or more of layer(s) 307 (e.g., support layer 418 (FIG. 4)) can be scored and/or embossed where multiple folds 308 are to be formed, such as, for example, to make mask structure 301 better able to receive multiple folds 308 and/or to guide folding of multiple folds 308 in mask structure 301. In these or other embodiments, one or more of layer(s) 307 (e.g., support layer 418 (FIG. 4)) can be scored where multiple folds 308 are to be formed in any suitable manner, including, for example, by a die press, a laser cutter, etc. Further, when layer(s) 307 comprise multiple layers (e.g., filtration layer 415 (FIG. 4) and support layer 418 (FIG. 4) and/or contact layer 421 (FIG. 4)) and when adjacent pairs of layer(s) 307 are coupled together by ultrasonic bonding, the bond lines can guide folding of multiple folds 308 in mask structure 301.

In some embodiments, when one or more of layer(s) 307 are impermeable to oxygen or air, mask structure 301, and more specifically, the one or more of layer(s) 307 that are impermeable to oxygen or air can comprise one or more apertures configured to permit oxygen or air to pass through the one or more of layer(s) 307 that are impermeable to oxygen or air. Accordingly, implementing the aperture(s) in the one or more of layer(s) 307 that are impermeable to oxygen or air can help to ensure that the one or more of layer(s) 307 that are impermeable to oxygen or air do not prevent respirator 300 from operating as a face-piece respirator. In these or other embodiments, the aperture(s) can be formed in any suitable manner, including, for example, by a die press, a laser cutter, etc. In many embodiments, the aperture(s) can be formed so as not to overlap multiple folds 308, but in other embodiments, at least part of the aperture(s) can overlap multiple folds 308. In some embodiments, the aperture(s) can be formed away from top side 311 to reduce fogging of ocular devices (e.g., goggles, glasses, etc.) being used by the user. Further, the aperture(s) can range in size from macroscopic to microscopic.

For example, in many embodiments, when support layer 418 (FIG. 4) is impermeable to oxygen or air, mask structure 301, and more specifically, support layer 418 (FIG. 4) can comprise respiration aperture(s) 324 to permit oxygen or air to pass through support layer 418 (FIG. 4). In other embodiments, respiration aperture(s) 324 can be omitted, such as, for example, when support layer 418 (FIG. 4) is omitted.

In many embodiments, multiple folds 308 can permit mask structure 301 to be stretched (e.g., similar to the folds of a bellows). In further embodiments, at least some of multiple folds 308 (i.e., one or more groups of plural folds) can be arranged to cause at least part of mask structure 301 to behave auxetically. For example, multiple folds 308 can comprise a first group of plural folds arranged in one or more waterbomb folding patterns, a second group of plural folds arranged in one or more Ron Resch folding patterns, a third group of plural folds arranged in one or more Miura-ori folding patterns, and/or one or more other groups of plural folds arranged in one or more other folding patterns configured to behave auxetically. Accordingly, the part or parts of mask structure 301 that the group(s) of plural folds cause to behave auxetically can expand in a direction that is approximately parallel to contact surface 609 (FIG. 6) and exterior surface 310 and that is approximately perpendicular to the direction of a stretching force applied to mask structure 301. In these or other embodiments, at least part of mask structure 301 (e.g., at least part of mask structure 301 that behaves auxetically) can comprise a negative Poisson ratio. The advantages of arranging at least some of multiple folds 308 to cause at least part of mask structure 301 to behave auxetically are described in greater detail below.

In many embodiments, as indicated above, respirator 300 can comprise right constraining mechanism 303 and/or left constraining mechanism 304. In these or other embodiments, right constraining mechanism 303 can constrain together mask structure 301 proximal to right side 312 (e.g., nearer to right side 312 than to the center of mask structure 301), bringing together mask structure 301 proximal to right side 312, and left constraining mechanism 304 can constrain mask structure 301 proximal to left side 314 (e.g., nearer to left side 313 than to the center of mask structure 301), bringing together mask structure 301 proximal to left side 314. For example, when multiple folds 308 comprise multiple horizontal folds, right constraining mechanism 303 can bring together mask structure 301 proximal to right side 312, causing the faces of the multiple horizontal folds to be brought approximately parallel to each other at right constraining mechanism 303, and left constraining mechanism 304 can bring together mask structure 301 proximal to left side 314, causing the faces of the multiple horizontal folds to be brought approximately parallel to each other at left constraining mechanism 304.

In implementation, right constraining mechanism 303 can comprise any suitable mechanism or mechanisms that can constrain mask structure 301 proximal to right side 312 to bring together mask structure 301 proximal to right side 312, and left constraining mechanism 304 can comprise any suitable mechanism or mechanisms that can constrain together mask structure 301 proximal to left side 314 to bring together mask structure 301 proximal to left side 314. In some embodiments, right constraining mechanism 303 can comprise a strap, a band, and/or thread wrapped around mask structure 301 proximal to right side 312. In these or other embodiments, when multiple folds 308 comprise multiple horizontal folds, right constraining mechanism 303 can comprise an adhesive applied to the faces of the multiple horizontal folds proximal to right side 312 to bond together the faces of the multiple horizontal folds. In these or other embodiments, right constraining mechanism 303 can comprise a clip and/or a clamp attached to mask structure 301 proximal to right side 312. Meanwhile, left constraining mechanism 304 can be similar or identical to right constraining mechanism 304 but with respect to left side 314 rather than right side 312. In some embodiments, such as, for example, when right constraining mechanism 303 and left constraining mechanism 304 are part of attachment mechanism 302, right constraining mechanism 303 can be part of left constraining mechanism 304, and vice versa.

In further embodiments, multiple folds 308 can be arranged such that mask structure 301 fans out toward left side 314 and away from right side 312 proximal to where mask structure 301 is constrained by right constraining mechanism 303 and/or such that mask structure 301 fans out toward right side 312 and away from left side 314 proximal to where mask structure 301 is constrained by left constraining mechanism 304. For example, mask structure 301 can fan out toward left side 314 and away from right side 312 at right constraining mechanism 303 when right constraining mechanism 303 comprises right adjustment mechanism 305 or when right adjustment mechanism 305 is omitted, and mask structure 301 can fan out toward right side 312 and away from left side 314 at left constraining mechanism 304 when left constraining mechanism 304 comprises left adjustment mechanism 306 or when left adjustment mechanism 306 is omitted. Meanwhile, mask structure 301 can fan out toward left side 314 and away from right side 312 at right adjustment mechanism 305 and near to right constraining mechanism 303 when right adjustment mechanism 305 is implemented separately from right constraining mechanism 303, and mask structure 301 can fan out toward right side 312 and away from left side 314 at left adjustment mechanism 306 and near to left constraining mechanism 304 when left adjustment mechanism 306 is implemented separately from left constraining mechanism 304.

In many embodiments, implementing right constraining mechanism 303 and left constraining mechanism 304 and arranging multiple folds 308 such that (i) mask structure 301 fans out toward left side 314 and away from right side 312 proximal to where mask structure 301 is constrained by right constraining mechanism 303 and (ii) mask structure 301 fans out toward right side 312 and away from left side 314 proximal to where mask structure 301 is constrained by left constraining mechanism 304 can cause mask structure 301 to curve in a generally synclastic manner about its center and with opposing bell shapes extending toward top side 311 and bottom side 313 so that mask structure 301 forms a dome at its center having contact surface 609 (FIG. 6) at its interior and exterior surface 310 at its exterior.

In many embodiments, implementing (i) right constraining mechanism 303 and left constraining mechanism 304 and/or (ii) multiple folds 308 can make mask structure 301 more rigid. For example, multiple folds 308 can function like a skeleton of mask structure 301, making mask structure 301 more rigid. Further, right constraining mechanism 303, left constraining mechanism 304, and multiple folds 308 can make mask structure 301 more rigid by causing mask structure 301 to form a dome such that forces applied to mask structure 301 can be distributed through mask structure 301 to right constraining mechanism 303 and left constraining mechanism 304.

In many embodiments, as indicated above, respirator 300 can comprise attachment mechanism 302. Attachment mechanism 302 can be coupled to mask structure 301. Further, when attachment mechanism 302 is coupled to mask structure 301, attachment mechanism 302 can be operable to couple mask structure 301 to a head of the user, such as, for example, as illustrated in FIG. 3. For example, attachment mechanism 302 can couple mask structure 301 to the face region of the user (e.g., over nostrils and/or a mouth of the face region of the user), and in some embodiments, to a submental region of the user. In these or other embodiments, the head of the user can be similar or identical to head 101 (FIG. 1); the face region of the user can be similar or identical to face region 102 (FIG. 1); the nostrils of the user can be similar or identical to nostrils 105 (FIG. 1); the mouth of the user can be similar or identical to mouth 103 (FIG. 1); and/or the submental region can be similar or identical to submental region 115 (FIG. 1). As discussed in greater detail below, when respirator 300 is coupled to the face region of the user over the nostrils and/or mouth of the face region of the user, respirator 300 can operate as a face-piece respirator to prevent or limit the user from inhaling one or more restricted substances. Meanwhile, in some embodiments, respirator 300 can prevent or limit other person(s) from inhaling one or more of the restricted substance(s) that may be exhaled by the user of respirator 300. In some embodiments, respirator 300 can be reusable one or more times and/or disposable.

Turning ahead in the drawings, FIG. 6 illustrates a rear view of respirator 300, according to the embodiment of FIG. 3. As indicated above, respirator 300 can comprise contact surface 609, right edge 632, left edge 633, top edge 634, and bottom edge 635. Right edge 632 can refer to an edge of mask structure 301 nearest to right side 312; left edge 633 can refer to an edge of mask structure 301 nearest to left side 311; top edge 634 can refer to an edge of mask structure 301 nearest to top edge 334; and bottom edge 635 can refer to an edge of mask structure 301 nearest to bottom side 313. Further, right edge 632 can be opposite of left edge 633, and vice versa; and top edge 634 can be opposite of bottom edge 635, and vice versa.

In many embodiments, contact region 609 can face toward the head of the user when mask structure 301 is coupled to the head of the user by attachment mechanism 302 (FIG. 3), and exterior surface 310 (FIG. 3) can face away from the head of the user when mask structure 301 is coupled to the head of the user by attachment mechanism

302 (FIG. 3). As a result, when attachment mechanism 302 couples mask structure 301 to the face region of the user over the nostrils and/or a mouth of the face region of the user, the dome formed in mask structure 301 by right constraining mechanism 303, left constraining mechanism 304, and multiple folds 308 can encircle and enclose the nostrils and/or the mouth of the face region of the user.

For example, in many embodiments, contact surface 609 can contact the face region of the user when mask structure 301 is coupled to the face region of the user. In these or other embodiments, contact surface 609 can contact a submental region of the user when mask structure 301 is coupled to the submental region of the user.

In these or other embodiments, when mask structure 301 is coupled to the face region of the user by attachment mechanism 302 (FIG. 3), multiple folds 308 (FIG. 3) can conform contact surface 609 to the face region of the user (i.e., bring contact surface 609 into direct contact with the skin of the face region of the user). In these or other embodiments, when mask structure 301 is coupled to the submental region of the user by attachment mechanism 302 (FIG. 3), multiple folds 308 (FIG. 3) can conform contact surface 609 to the submental region of the user (i.e., bring contact surface 609 into direct contact with the skin of the submental region of the user). For example, when at least some of multiple folds 308 (FIG. 3) are arranged to cause at least part of mask structure 301 to behave auxetically, and when mask structure is coupled to the face region and/or the submental region of the user by attachment mechanism 302 (FIG. 3), stretching forces applied to mask structure 301 by attachment mechanism 302 (FIG. 3) can drive contact surface 609 into contact with the face region and/or the submental region of the user as a result of the auxetic behavior of mask structure 301.

Meanwhile, by conforming contact surface 609 to the face region of the user, and when applicable, to the submental region of the user, multiple folds 308 (FIG. 3) can cause contact surface 609 to form a mechanical seal partly or entirely around the nostrils and/or the mouth of the face region of the user with the face region, and when applicable, with the submental region of the user. For example, in some embodiments, when mask structure 301 is coupled to the face region of the user by attachment mechanism 302 (FIG. 3), multiple folds 308 (FIG. 3) can conform and thereby mechanically seal contact surface 609 to the face region of the user over at least a nasal bone, a maxilla bone, and/or a mandible bone of the user. In these or other embodiments, when mask structure 301 is coupled to the face region of the user by attachment mechanism 302, multiple folds 308 (FIG. 3) can conform and thereby mechanically seal contact surface 609 to the face region of the user over a right frontal process of the maxilla bone and a left frontal process of the maxilla bone of the user. In further embodiments, when mask structure 301 is coupled to the face region of the user by attachment mechanism 302, multiple folds 308 (FIG. 3) can conform and thereby mechanically seal contact surface 609 to the face region of the user over a right zygomatic bone and/or a left zygomatic bone of the user. In still further embodiments, when mask structure 301 is coupled to the submental region of the user by attachment mechanism 302, multiple folds 308 (FIG. 3) can conform and thereby mechanically seal contact surface 609 to the submental region of the user. In many embodiments, the nasal bone can be similar or identical to nasal bone 207 (FIG. 2); the maxilla bone can be similar or identical to maxilla bone 208 (FIG. 2); the mandible bone can be similar or identical to mandible bone 211 (FIG. 2); the right frontal process of the maxilla bone of the user can be similar or identical to right frontal process 212 (FIG. 2); the left frontal process of the maxilla bone of the user can be similar or identical to left frontal process 213 (FIG. 2); the right zygomatic bone of the user can be similar or identical to right zygomatic bone 209 (FIG. 2); and the left zygomatic bone of the user can be similar or identical to left zygomatic bone 210 (FIG. 2).

In many embodiments, respirator 300 can better prevent or limit the user and/or one or more other persons from inhaling one or more restricted substances as a result of the mechanical seal that contact surface 609 can form with the face region of the user, and when applicable, with the submental region of the user. For example, because contact surface 609 is able conform to and form a mechanical seal with the face region of the user over the right frontal process and the left frontal process of the maxilla bone of the user, contact surface 609 can form a mechanical seal around the ridge of the nose of the user, as distinguished from conventional respirators that may span from the nasal bone down to the maxilla bone without contacting the right frontal process and the left frontal process of the maxilla bone. Meanwhile, because contact surface 609 is able to conform to and form a mechanical seal with the submental region of the user, respirator 300 is able to form a mechanical seal around the nostrils and/or the mouth of the face region of the user even where respirator 300 extends below a chin of the user. The chin can be similar or identical to chin 114 (FIG. 1). Also, because multiple folds 308 (FIG. 3) drive contact surface 609 into the face region of the user, and when applicable, into the submental region of the user, the mechanical seal that contact surface 609 can form with the face region of the user, and when applicable, with the submental region of the user can adapt to changing contours of the face region and/or submental region, such as, for example, resulting from jaw movements of the user.

Further, implementing respirator 300 with multiple folds 308 and/or such that a dome is formed in mask structure 301 by right constraining mechanism 303, left constraining mechanism 304, and multiple folds 308, as described above, can advantageously increase an effective portion of mask structure 301. The effective portion of mask structure 301 can refer to a portion of mask structure 301 through which the user can receive oxygen or air when attachment mechanism 302 is coupling mask structure 301 to the face region of the user over nostrils and/or a mouth of the face region of the user. For example, in many embodiments, the effective portion of mask structure 301 can comprise a portion of mask structure 301 inside of the mechanical seal that contact surface 609 (FIG. 6) forms with the face region of the user, and in some embodiments, with the submental region of the user. Increasing the effective portion of mask structure 301 can reduce breathing resistance to the user when inhaling oxygen or air through respirator 300, resulting in greater comfort to the user when using respirator 300. Also, increasing the effective portion of mask structure 301 can permit implementation of filtration material(s) of filtration layer 415 (FIG. 4) having greater filtering capability (i.e., higher filtration efficiency) but also higher breathing resistance to the user when inhaling oxygen or air through respirator 300. Further, increasing the effective portion of mask structure 301 can extend a life of respirator 300 because the increased effective portion of mask structure 301 will take more time to become fully embedded with filtered restricted substance(s).

In these or other embodiments, the effective portion of mask structure 301 can comprise an effective portion exterior surface area at exterior surface 310. In many embodiments, the effective portion exterior surface area can be greater than or equal to approximately 103.2 square centimeters.

Further still, respirator 300 can comprise a respirator efficiency. In many embodiments, implementing respirator 300 with multiple folds 308 and/or such that a dome is formed in mask structure 301 by right constraining mechanism 303, left constraining mechanism 304, and multiple folds 308, as described above, can advantageously increase the respirator efficiency of respirator 300. For example, in some embodiments, the respirator efficiency of respirator 300 can be greater than or equal to approximately 1/50, 1/55, 1/60, or 1/65.

Even further still, in some embodiments, implementing respirator 300 with multiple folds 308 and/or such that a dome is formed in mask structure 301 by right constraining mechanism 303, left constraining mechanism 304, and multiple folds 308, as described above, can advantageously maintain separation between contact surface 609 (FIG. 6) and the nostrils and/or the mouth of the face region of the user when respirator 300 is being used. As a result, contamination of contact surface 609 (FIG. 6) can be reduced and the user can more easily speak when using respirator 300.

Also, in some embodiments, implementing respirator 300 with multiple folds 308 and/or such that a dome is formed in mask structure 301 by right constraining mechanism 303, left constraining mechanism 304, and multiple folds 308, as described above, can advantageously allow for respirator 300 to be implemented without a gasket at contact surface 609 (FIG. 6). For example, in these embodiments, the mechanical seal that contact surface 609 (FIG. 6) forms around the nostrils and/or the mouth of the face region of the user with the face region, and when applicable, with the submental region of the user may obviate a need for a gasket. Meanwhile, because the gasket can be omitted from contact surface 609 (FIG. 6), respirator 300 can be more comfortable for the user.

In many embodiments, the mechanical seal that contact surface 609 forms around the nostrils and/or the mouth of the face region of the user with the face region, and when applicable, with the submental region of the user can comprise a mechanical seal shape. For example, the mechanical seal shape can comprise part or all of an elliptical shape, an egg curve shape, or a pear curve shape.

In some embodiments, configuring contact layer 421 (FIG. 4) to provide capillary action to wick away moisture at first contact layer surface 422 (FIG. 4) when contact layer 421 (FIG. 4) is implemented, or configuring filtration layer 415 (FIG. 4) to provide capillary action to wick away moisture at first filtration layer surface 416 (FIG. 4) when contact layer 421 (FIG. 4) is omitted, can permit mask structure 301 to pull moisture away from the face region and/or submental region of the user when mask structure 301 is coupled to the face region and/or submental region of the user and contact surface 609 is contacting the face region and/or submental region of the user. In further embodiments, when contact layer 421 (FIG. 4) is implemented, contact layer 421 (FIG. 4) can be referred to as a scrim layer, such as, for example, because contact layer 421 (FIG. 4) can act as a buffer between filtration layer 415 (FIG. 4) and the face region and/or submental region of the user when mask structure 301 is coupled to the face region and/or submental region of the user. In these or other embodiments, contact layer 421 (FIG. 4) can be configured so as to more comfortably interface with the face region and/or submental region of the user than the filtration layer 415 (FIG. 4).

In many embodiments, at least part of right edge 632 and/or left edge 633 can be scalloped. For example, scalloping part or all of right edge 632 and/or left edge 633 can diminish or remove sharp corners that might otherwise form at right edge 632 and/or left edge 633 as a result of constraining mask structure 301 with right constraining mechanism 303 (FIG. 3) and/or left constraining mechanism 304 (FIG. 3), thereby preventing mask structure 301 from digging into the face region of the user at right side 312 (FIG. 3) and/or left side 314 (FIG. 3) when mask structure 301 is coupled to the face region of the user by attachment mechanism 302 (FIG. 3). As a result, scalloping right edge 632 and/or left edge 633 can increase the comfort of the user when using respirator 300.

Referring now back to FIG. 3, in many embodiments, as indicated above, respirator 300 can comprise malleable band(s) 325. Malleable band(s) 325 can be coupled to and/or embedded within mask structure 301 and can be operably bent by the user to further conform contact surface 609 to the face region of the user, and when applicable, to the submental region of the user. In implementation, malleable band(s) 325 can comprise one or more flexible metal bands. In these or other embodiments, malleable band(s) 325 can comprise nose malleable band 331, which can be located over the nose of the face region of the user. Nose malleable band 331 can be operably bent by the user to further conform contact surface 609 (FIG. 6) to the face region of the user over the nasal bone, the right frontal process of the maxilla bone, and the left frontal process of the maxilla bone of the user. In some embodiments, nose malleable band 331 can be referred to as a nose clip. However, in other embodiments, respirator 300 can be devoid of malleable band(s) 325 (e.g., nose malleable band 331). For example, because contact surface 609 is able conform to and form a mechanical seal with the face region of the user over the right frontal process and the left frontal process of the maxilla bone of the user without nose malleable band 331, nose malleable band 331 can be omitted. Because malleable band(s) 325 can be omitted from respirator 300, respirator 300 can be made lighter and more comfortable to use.

In many embodiments, as indicated above, respirator 300 can comprise exhalation valve(s) 326. Exhalation valve(s) 326 can comprise one or more one-way valves passing through one or more of layer(s) 307. Exhalation valve(s) 326 can channel gas or gases exhaled by the user out through exhalation valve(s) 326 when attachment mechanism 302 is coupling mask structure 301 to the face region of the user over nostrils and/or a mouth of the face region of the user. As a result, exhalation valve(s) 326 can minimize the presence of gas or gases exhaled by the user when the user inhales a next breath.

In some embodiments, exhalation valve(s) 326 can have an input at contact surface 609 (FIG. 6) and an output at exterior surface 310. In further embodiments, one or more of the input(s) of exhalation valve(s) 326 can be embedded in mask structure 301 and located at filtration layer first surface 416 or support layer first surface 419, such as, for example, as illustrated at FIG. 6. Meanwhile, in these or other embodiments, one or more of the output of exhalation valve(s) 326 can be embedded in mask structure 301 and located at filtration layer second surface 417 or contact layer second surface 423.

In implementation, exhalation valve(s) 326 can comprise one or more flapper valves and/or one or more butterfly valves. In some embodiments, exhalation valve(s) 326 can be riveted, welded, and/or adhered to mask structure 301.

In other embodiments, exhalation valve(s) 326 can be omitted. For example, in various embodiments, because of the increased effective portion of respirator 300, as described above, gas or gases exhaled by the user can more easily exit respirator 300, reducing a need for exhalation valve(s) 326.

In many embodiments, multiple folds 308 can permit mask structure 301 to be collapsed under applied pressure. Collapsing mask structure 301 can permit respirator 300 to be densely packaged in shrink-wrap, taking up less retail shelf space. Meanwhile, tension applied to mask structure 301 by right constraining mechanism 303 and/or left constraining mechanism 304 can cause mask structure 301 to self-expand when the applied pressure (e.g., packaging) is removed. The spring force with which mask structure 301 self expands can depend on the width or widths of the fold lines of multiple folds 308 relative to the filtration layer thickness of filtration layer 415 (FIG. 4), and when applicable, to the support layer thickness of support layer 418 (FIG. 4) and/or the contact layer thickness of contact layer 421 (FIG. 4). The spring force with which mask structure 301 self expands increases as the width(s) of the fold lines of multiple folds 308 decreases relative to the filtration layer thickness of filtration layer 415 (FIG. 4), and when applicable, to the support layer thickness of support layer 418 (FIG. 4) and/or the contact layer thickness of contact layer 421 (FIG. 4). Meanwhile, the spring force with which mask structure 301 self expands decreases as the width(s) of the fold lines of multiple folds 308 increases relative to the filtration layer thickness of filtration layer 415 (FIG. 4), and when applicable, to the support layer thickness of support layer 418 (FIG. 4) and/or the contact layer thickness of contact layer 421 (FIG. 4).

Further, in these or other embodiments, multiple folds 308 can permit mask structure 301 to be folded (e.g., in half) bringing contact surface 609 (FIG. 6) into contact with itself. For example, in some embodiments, multiple folds 308 can permit mask structure 301 to be folded (e.g., in half) about the y-axis of the Cartesian coordinate system having an origin at a center point of mask structure 301. As a result, contact surface 609 (FIG. 6) can be protected from contamination when respirator 300 is not being used, which can make respirator 300 more hygienic for the user when respirator 300 is being used. Meanwhile, because multiple folds 308 can permit mask structure 301 to be folded (e.g., in half) to bring contact surface 609 (FIG. 6) into contact with itself, respirator 300 can be made more compact for storage purposes.

In some embodiments, right constraining mechanism 303 and/or left constraining mechanism 304 can facilitate mask structure 301 being folded (e.g., in half) to bring contact surface 609 (FIG. 6) into contact with itself. For example, right constraining mechanism 303, by constraining mask structure 301 proximal to right side 312 to bring together mask structure 301 proximal to right side 312, and left constraining mechanism 304, by constraining together mask structure 301 proximal to left side 314 to bring together mask structure 301 proximal to left side 314, can help to guide mask structure 301 into the folded (e.g., in half) configuration when forces are applied to mask structure 301 approximately perpendicular to the y-axis of the Cartesian coordinate system having an origin at a center point of mask structure 301 such that contact surface 609 comes together cleanly and consistently about the y-axis.

In further embodiments, when mask structure 301 is folded (e.g., in half) bringing contact surface 609 (FIG. 6) into contact with itself, attachment mechanism 302 can be wrapped around mask structure 301 to hold mask structure 301 in the folded (e.g., in half) configuration. In these or other embodiments, when mask structure 301 is folded (e.g., in half) bringing contact surface 609 (FIG. 6) into contact with itself, mask structure 301 can be held in the folded (e.g., in half) configuration by a clasp, such as, for example, a magnetic clasp. In these embodiments, respirator 300 and/or mask structure 301 can comprise the clasp. In some embodiments, the clasp can be permanently coupled to respirator 300 and/or mask structure 301 and operable to hold mask structure 301 in the folded (e.g., in half) configuration. In other embodiments, the clasp can be removably coupled to respirator 300 and/or mask structure 301 to hold mask structure 301 in the folded (e.g., in half) configuration.

In many embodiments, such as, for example, when support layer 418 (FIG. 4) is implemented, exterior surface 310 can be printed with color and/or designs. Printing exterior surface 310 with color and/or designs can make respirator 300 more aesthetically pleasing to the user.

In many embodiments, as indicated above, mask structure 301 can comprise right adjustment mechanism 305 and/or left adjustment mechanism 306. Right adjustment mechanism 305 and/or left adjustment mechanism 306 can be operable to control where at contact surface 609 (FIG. 6) that contact surface 609 (FIG. 6) contacts the face region of the user when mask structure 301 is coupled to the face region of the user by attachment mechanism 302. In these or other embodiments, right adjustment mechanism 305 and/or left adjustment mechanism 306 can be operable to control where at contact surface 609 (FIG. 6) that contact surface 609 (FIG. 6) contacts the submental region of the user when mask structure 301 is coupled to the submental region of the user by attachment mechanism 302. In other words, right adjustment mechanism 305 and/or left adjustment mechanism 306 can be operable to adjust a size of the mechanical seal that contact surface 609 (FIG. 6) forms around the nostrils and/or the mouth of the face region of the user with the face region, and when applicable, with the submental region of the user. As a result, right adjustment mechanism 305 and/or left adjustment mechanism 306 can adjust to the user a fit of respirator 300.

In some embodiments, right adjustment mechanism 305 and/or left adjustment mechanism 306 can be operable to be repositioned (e.g., slid) along exterior surface 310 to control where at contact surface 609 (FIG. 6) that contact surface 609 (FIG. 6) contacts the face region of the user, and when applicable, the submental region of the user when mask structure 301 is coupled to the face region of the user, and when applicable, to the submental region of the user. For example, in various embodiments, right adjustment mechanism 305 and/or left adjustment mechanism 306 can be repositioned (e.g., slid) along exterior surface 310 toward or away from the center of mask structure 301. Reposition (e.g., sliding) right adjustment mechanism 305 and/or left adjustment mechanism 306 toward the center of mask structure 306 can decrease a curvature of the opposing bell shapes forming the dome in mask structure 301 by right constraining mechanism 303, left constraining mechanism 304, and multiple folds 308, thereby increasing a size of the dome. Meanwhile, repositioning (e.g., sliding) right adjustment mechanism 305 and/or left adjustment mechanism 306 away from the center of mask structure 306 can increase a curvature of the opposing bell shapes forming the dome in mask structure 301 by right constraining mechanism 303, left constraining mechanism 304, and multiple folds 308, thereby decreasing a size of the dome.

In implementation, right adjustment mechanism 305 can comprise any suitable mechanism that can control where at contact surface 609 (FIG. 6) that contact surface 609 (FIG. 6) contacts the face region of the user, and when applicable, the submental region of the user when mask structure 301 is coupled to the face region of the user, and when applicable, to the submental region of the user; and left constraining mechanism 304 can comprise any suitable mechanism that can control where at contact surface 609 (FIG. 6) that contact surface 609 (FIG. 6) contacts the face region of the user, and when applicable, the submental region of the user when mask structure 301 is coupled to the face region of the user, and when applicable, to the submental region of the user. For example, in some embodiments, right adjustment mechanism 303 can comprise a strap, a band, or thread wrapped around mask structure 301 proximal to right side 312. In other embodiments, right adjustment mechanism 303 can comprise a clip or a clamp attached to mask structure 301 proximal to right side 312. The strap, band, threads, clip, or clamp can be configured to be repositioned along exterior surface 310 to control where at contact surface 609 (FIG. 6) that contact surface 609 (FIG. 6) contacts the face region of the user when mask structure 301 is coupled to the face region of the user by attachment mechanism 302. Meanwhile, left adjustment mechanism 306 can be similar or identical to right adjustment mechanism 305 but with respect to left side 314 rather than right side 312.

In some embodiments, such as, for example, when right adjustment mechanism 305 and left adjustment mechanism 306 are part of attachment mechanism 302, right adjustment mechanism 305 can be part of left adjustment mechanism 306, and vice versa. In these or other embodiments, right constraining mechanism 303 can be part of right adjustment mechanism 305, and/or left constraining mechanism 304 can be part of left adjustment mechanism 306. In other embodiments, right adjustment mechanism 305 can be separate from right constraining mechanism 303, and/or left adjustment mechanism 306 can be separate from left constraining mechanism 304. When right adjustment mechanism 305 is separate from right constraining mechanism 303, right adjustment mechanism 305 can be located between right constraining mechanism 303 and the center of mask structure 301, and in many embodiments, closer to right constraining mechanism 303 than to the center of mask structure 301. Meanwhile, when left adjustment mechanism 306 is separate from left constraining mechanism 304, left adjustment mechanism 306 can be located between left constraining mechanism 304 and the center of mask structure 301, and in many embodiments, closer to left constraining mechanism 304 than to the center of mask structure 301.

Figure 7:
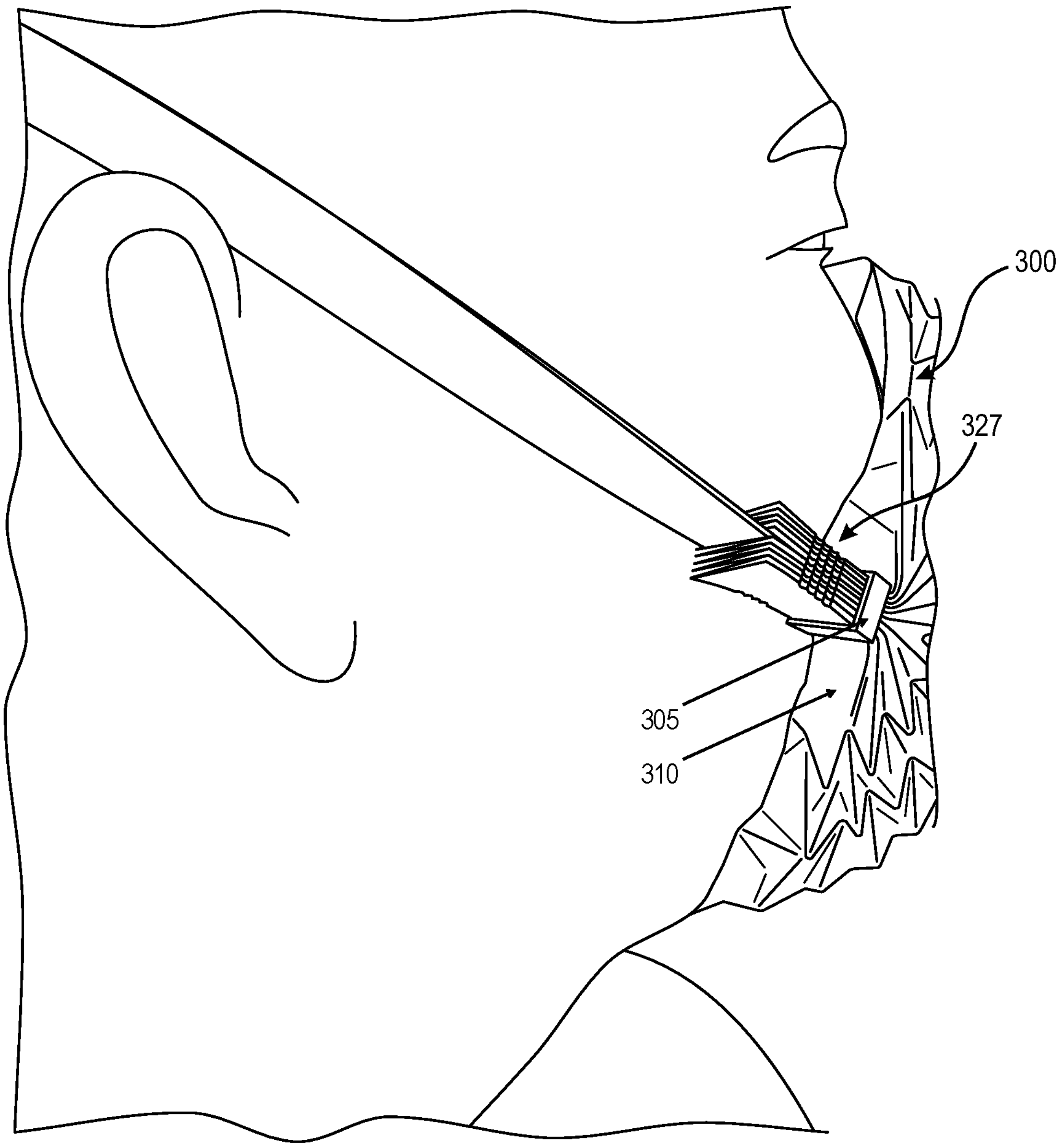
FIG. 7 illustrates a right side view of the respirator, including one or more right adjustment mechanism stops of the respirator, according to the embodiment of FIG. 3.

Turning ahead in the drawings, FIG. 7 illustrates a right side view of respirator 300, including right adjustment mechanism stop(s) 327, according to the embodiment of FIG. 3. In many embodiments, as indicated above, respirator 300 can comprise right adjustment mechanism stop(s) 327 and/or left adjustment mechanism stop(s) 328 (FIG. 3). Right adjustment mechanism stop(s) 327 can be implemented when right adjustment mechanism 305 is implemented, and left adjustment mechanism stop(s) 328 (FIG. 3) can be implemented when left adjustment mechanism 306 (FIG. 3) is implemented.

Right adjustment mechanism stop(s) 327 can comprise one or more mechanisms configured to hold right adjustment mechanism 305 stationary at various different positions along exterior surface 310 where right adjustment mechanism 305 is configured to be operably repositioned. Each right adjustment mechanism stop of right adjustment mechanism stop(s) 327 can receive right adjustment mechanism 305 at different times, and can hold right adjustment mechanism 305 stationary until it is desirable to reposition right adjustment mechanism 305. In implementation, right adjustment stop(s) 327 can comprise one or more notches or dimples formed in mask structure 301. In many embodiments, left adjustment stop(s) 328 can be similar or identical to right adjustment stop(s) 327 but with respect to left adjustment mechanism 306 (FIG. 3). In other embodiments, right adjustment mechanism stop(s) 327 and/or left adjustment mechanism stop(s) 328 can be omitted.

Referring back to FIG. 3, attachment mechanism 302 can comprise any suitable mechanism configured to be coupled to mask structure 301 and configured to couple mask structure 301 to the head (e.g., face region and/or submental region) of the user. For example, attachment mechanism 302 can comprise a harness configured to be coupled to mask structure 301 and configured to coupled mask structure 301 to the head (e.g., face region and/or submental region) of the user. In many embodiments, a tightness with which attachment mechanism 302 couples mask structure 301 to the head (e.g., face region and/or submental region) of the user can be adjusted. Adjusting the tightness with which attachment mechanism 302 couples mask structure 301 to the head (e.g., face region and/or submental region) of the user can adjust the pressure with which contact surface 609 (FIG. 6) forms a mechanical seal with the face region of the user, and when applicable, with the submental region of the user.

In many embodiments, attachment mechanism 302 can be coupled to mask structure 301 proximal to right side 312 and proximal to left side 311. Attachment mechanism 302 can be coupled to mask structure 301 in any suitable manner, such as, for example, ultrasonic bonding, stapling, adhering, or sewing. In these or other embodiments, attachment mechanism 302 can be threaded through one or more apertures formed in mask structure 301.

In some embodiments, when right constraining mechanism 303 is implemented, and when right constraining mechanism 303 is separate from attachment mechanism 302, attachment mechanism 302 can be coupled to mask structure 301 proximal to right side 312, such as, for example, between right edge 632 (FIG. 6) and right constraining mechanism 303. Meanwhile, when left constraining mechanism 304 is implemented, and when left constraining mechanism 304 is separate from attachment mechanism 302, attachment mechanism 302 can be coupled to mask structure 301 proximal to left side 311, such as, for example, between left edge 633 (FIG. 6) and left constraining mechanism 304.

In further embodiments, such as, for example, when right constraining mechanism 303 is implemented, when right adjustment mechanism 305 is implemented, when right constraining mechanism 303 is part of attachment mechanism 302, and when right adjustment mechanism 305 is part of right constraining mechanism 303, attachment harness 302 can be coupled to mask structure 301 at one of various first apertures formed in mask structure 301 between right side 312 and the center of mask structure 301 and at one of various second apertures formed in mask structure 301 between left side 314 and the center of mask structure 301. For example, threading attachment mechanism 302 through one of each of the first and second apertures can function to constrain mask structure 301 proximal to right side 312 and left side 314. Meanwhile, repositioning attachment mechanism 302 between or among the first apertures and between or among the second apertures can function to reposition attachment mechanism 302 along exterior surface 310.

In many embodiments, as illustrated at FIG. 3, attachment mechanism 302 can comprise a harness having a first strap coupled to mask structure 301 proximal to right side 312 and a second strap coupled to mask structure 301 proximal to left side 314. In these embodiments, the first and second strap can be wrapped around the head of the user over the right and left ears of the user, and tied or clipped together behind the head of the user. The right ear can be similar or identical to right ear 116 (FIG. 1), and the left ear can be similar or identical to left ear 117 (FIG. 1).

Figure 8:
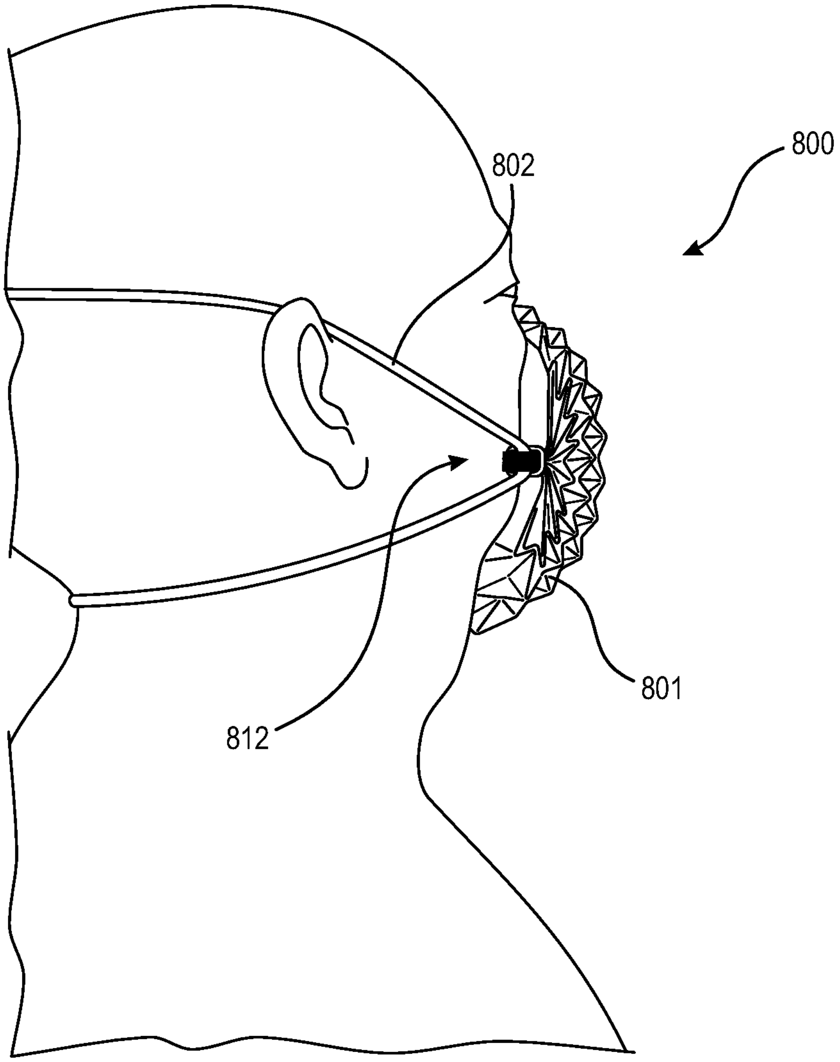
FIG. 8 illustrates a respirator, according to an embodiment.

Turning ahead in the drawings, FIG. 8 illustrates a respirator 800, according to an embodiment. Respirator 800 can comprise mask structure 801, attachment mechanism 802, right side 812, and a left side (not shown). Meanwhile, mask structure 801 can be similar or identical to mask structure 301 (FIG. 3), attachment mechanism 802 can be similar or identical to attachment mechanism 302 (FIG. 3), right side 812 can be similar or identical to right side 312 (FIG. 3), and the left side can be similar or identical to left side 314 (FIG. 3).

In many embodiments, attachment mechanism 802 can comprise a harness having a single strap. The single strap can wrap behind a head of the user, over (or under (not shown)) the right and left ears of the user. Further, the single strap can be coupled to mask structure 301 proximal to right side 812 and the left side of respirator 800 and then wrapped back behind the head of the user, under the right and left ears of the user, where the ends of the single strap can be tied or clipped together. The head can be similar to head 101 (FIG. 1), the right ear can be similar or identical to right ear 116 (FIG. 1), and the left ear can be similar or identical to left ear 117 (FIG. 1).

Figure 9:
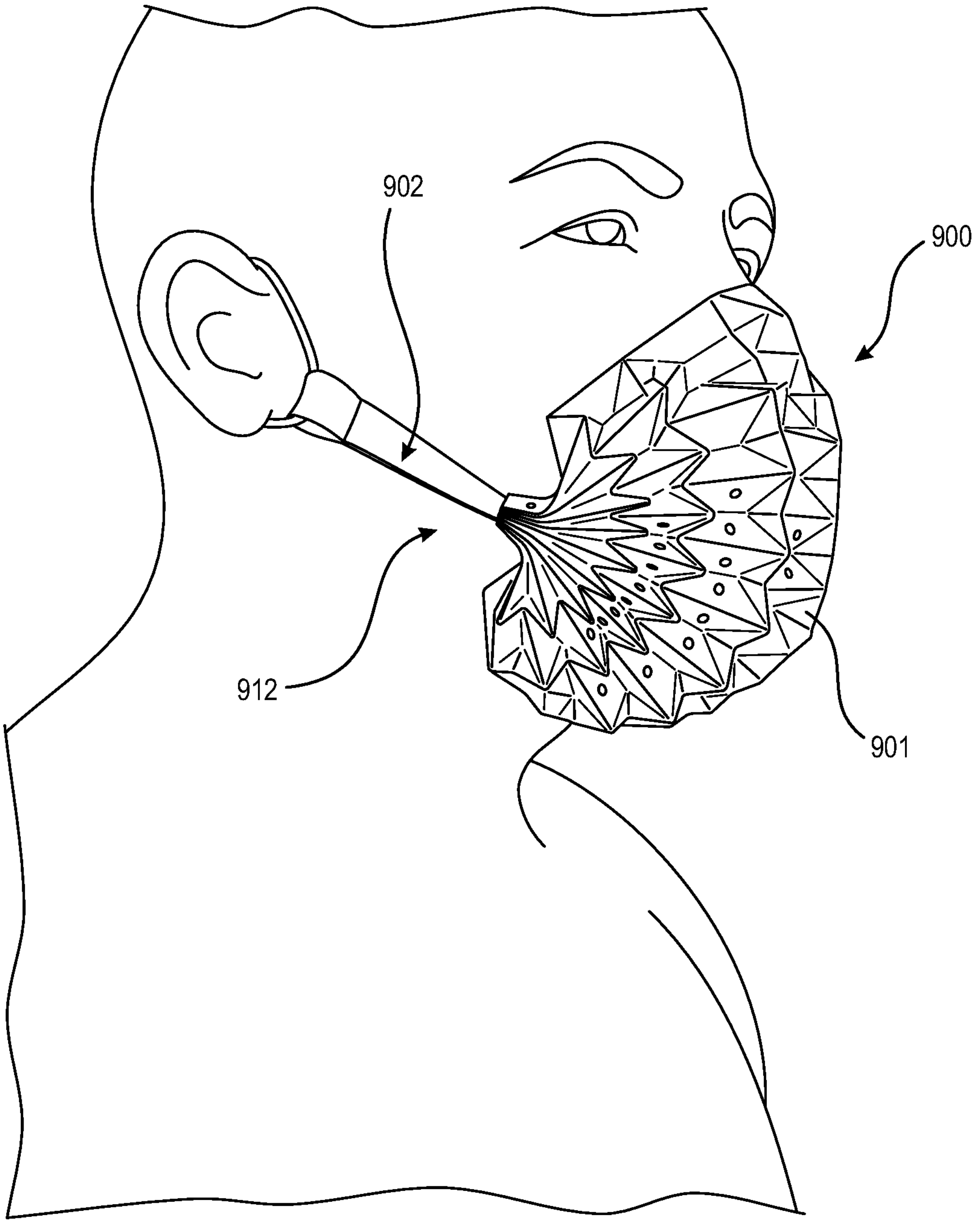
FIG. 9 illustrates a respirator, according to an embodiment.

Turning ahead in the drawings, FIG. 9 illustrates a respirator 900, according to an embodiment. Respirator 900 can comprise mask structure 901, attachment mechanism 902, right side 912, and a left side (not shown). Meanwhile, mask structure 901 can be similar or identical to mask structure 301 (FIG. 3) and/or mask structure 801 (FIG. 1), attachment mechanism 902 can be similar or identical to attachment mechanism 302 (FIG. 3) and/or attachment mechanism 802 (FIG. 2), right side 812 (FIG. 8) can be similar or identical to right side 312 (FIG. 3) and/or right side 812 (FIG. 8), and the left side can be similar or identical to left side 314 (FIG. 3) and/or the left side of respirator 800 (FIG. 8).

In many embodiments, attachment mechanism 902 can comprise a harness having a first strap coupled to mask structure 901 proximal to right side 912 and a second strap coupled to mask structure 301 proximal to the left side of respirator 900. In these embodiments, the first strap can comprise a first loop wrapped around the right ear of the user, and the second strap can comprise a second loop wrapped around the left ear of the user. The right ear can be similar or identical to right ear 116 (FIG. 1), and the left ear can be similar or identical to left ear 117 (FIG. 1).

Figure 10:
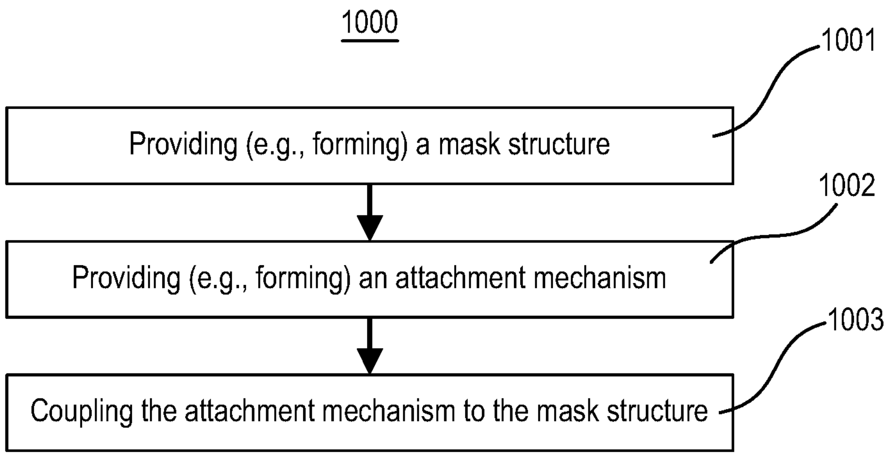
FIG. 10 illustrates a flow chart for an embodiment of a method of providing (e.g., manufacturing) a respirator.

FIG. 10 illustrates a flow chart for an embodiment of a method 1000 of providing (e.g., manufacturing) a respirator. The respirator can be similar or identical to respirator 300 (FIG. 3), respirator 800 (FIG. 8), and/or respirator 900 (FIG. 9). Method 1000 is merely exemplary and is not limited to the embodiments presented herein. Method 1000 can be employed in many different embodiments or examples not specifically depicted or described herein. In some embodiments, the activities of method 1000 can be performed in the order presented. In other embodiments, the activities of method 1000 can be performed in any other suitable order. In still other embodiments, one or more of the activities in method 1000 can be combined or skipped.

In many embodiments, method 1000 can comprise activity 1001 of providing (e.g., forming) a mask structure. In some embodiments, performing activity 1001 can be similar or identical to providing (e.g., forming) mask structure 301 (FIG. 3), mask structure 801 (FIG. 8), and/or mask structure 901 (FIG. 9), as described above. Further, the mask structure can be similar or identical to mask structure 301 (FIG. 3), mask structure 801 (FIG. 8), and/or mask structure 901 (FIG. 9).

In many embodiments, method 1000 can comprise activity 1002 of providing (e.g., forming) an attachment mechanism. In some embodiments, performing activity 1002 can be similar or identical to providing (e.g., forming) attachment mechanism 302 (FIG. 3), attachment mechanism 802 (FIG. 8), and/or attachment mechanism 902 (FIG. 9), as described above. Further, the attachment mechanism can be similar or identical to attachment mechanism 302 (FIG. 3), attachment mechanism 802 (FIG. 8), and/or attachment mechanism 902 (FIG. 9).

In many embodiments, method 1000 can comprise activity 1003 of coupling the attachment mechanism to the mask structure. In some embodiments, performing activity 1003 can be similar or identical to coupling the attachment mechanism to the mask structure as described above with respect to respirator 300 (FIG. 3).

Although the invention has been described with reference to specific embodiments, it will be understood by those skilled in the art that various changes may be made without departing from the spirit or scope of the disclosure. Accordingly, the disclosure of embodiments is intended to be illustrative of the scope of the disclosure and is not intended to be limiting. It is intended that the scope of the disclosure shall be limited only to the extent required by the appended claims. For example, to one of ordinary skill in the art, it will be readily apparent that any element of FIGS. 1-10 may be modified, and that the foregoing discussion of certain of these embodiments does not necessarily represent a complete description of all possible embodiments. For example, one or more of the activities of method 1000 (FIG. 10) or one or more of the other methods described herein may include different activities and be performed by many different systems and/or in many different orders.

Generally, replacement of one or more claimed elements constitutes reconstruction and not repair. Additionally, benefits, other advantages, and solutions to problems have been described with regard to specific embodiments. The benefits, advantages, solutions to problems, and any element or elements that may cause any benefit, advantage, or solution to occur or become more pronounced, however, are not to be construed as critical, required, or essential features or elements of any or all of the claims, unless such benefits, advantages, solutions, or elements are stated in such claim.

Moreover, embodiments and limitations disclosed herein are not dedicated to the public under the doctrine of dedication if the embodiments and/or limitations: (1) are not expressly claimed in the claims; and (2) are or are potentially equivalents of express elements and/or limitations in the claims under the doctrine of equivalents.

What is claimed is:

1. A respirator comprising:
a mask structure comprising:
one or more layers;
multiple folds;
a contact surface region;
a left side; and
a right side opposite the left side;
an attachment mechanism coupled to the mask structure, the attachment mechanism being operable to couple the mask structure to a face region of a user;
a first fit adjustment mechanism;
a first constraining mechanism; and
a second constraining mechanism;
wherein:
the one or more layers comprise a filtration layer;
the mask structure is constrained together proximal to the left side by the first constraining mechanism;
the mask structure is constrained together proximal to the right side by the second constraining mechanism;
the multiple folds are arranged such that the mask structure fans out toward the right side proximal to where the mask structure is constrained by the first constraining mechanism and the mask structure fans out toward the left side proximal to where the mask structure is constrained by the second constraining mechanism;
when the mask structure is coupled to the face region of the user by the attachment mechanism, the contact surface region is operable to contact the face region of the user; and
the first fit adjustment mechanism is operable to control where at the contact surface region that the contact surface region contacts the face region of the user when the mask structure is coupled to the face region of the user by the attachment mechanism.

2. The respirator of claim 1 wherein:
the attachment mechanism comprises at least one of the first constraining mechanism or the second constraining mechanism.

3. The respirator of claim 1 wherein:
the first constraining mechanism comprises the first fit adjustment mechanism.

4. The respirator of claim 1 wherein:
the mask structure comprises an exterior surface region; and
the first fit adjustment mechanism is operable to be repositioned along the exterior surface region to control where at the contact surface region that the contact surface region contacts the face region of the user when the mask structure is coupled to the face region of the user by the attachment mechanism.

5. The respirator of claim 1 further comprising:
a second fit adjustment mechanism;
wherein:
the second fit adjustment mechanism is operable to control where at the contact surface region that the contact surface region contacts the face region of the user when the mask structure is coupled to the face region of the user by the attachment mechanism.

6. The respirator of claim 5 wherein:
the second constraining mechanism comprises the second fit adjustment mechanism.

7. The respirator of claim 5 wherein:
the first fit adjustment mechanism comprises the second fit adjustment mechanism.

8. The respirator of claim 5 wherein:
at least one of:
the first constraining mechanism comprises the first fit adjustment mechanism; or
the second constraining mechanism comprises the second fit adjustment mechanism;
and
the attachment mechanism comprises at least one of the first constraining mechanism or the second constraining mechanism.

9. The respirator of claim 5 wherein:
the attachment mechanism comprises at least one of the first fit adjustment mechanism or the second fit adjustment mechanism.

10. The respirator of claim 1 wherein:
the mask structure comprises:
a left edge proximal to the left side; and
a right edge proximal to the right side;
and
at least part of at least one of the left edge or the right edge is scalloped.

11. The respirator of claim 1, wherein:
the multiple folds are arranged to cause at least part of the mask structure to behave auxetically.

12. The respirator of claim 1 wherein:
when the mask structure is coupled to the face region of the user by the attachment mechanism, the contact surface region is operable to automatically conform to the face region of the user.

13. A respirator comprising:
a mask structure comprising:
multiple folds;
a contact surface region;
a left side; and
a right side opposite the left side;
an attachment mechanism coupled to the mask structure, the attachment mechanism being operable to couple the mask structure to a face region of a user;
a first fit adjustment mechanism;
a first constraining mechanism; and
a second constraining mechanism,
wherein:
the mask structure is constrained together proximal to the left side by the first constraining mechanism;
the mask structure is constrained together proximal to the right side by the second constraining mechanism;
the multiple folds are arranged such that the mask structure fans out toward the right side proximal to where the mask structure is constrained by the first constraining mechanism and the mask structure fans out toward the left side proximal to where the mask structure is constrained by the second constraining mechanism;
when the mask structure is coupled to the face region of the user by the attachment mechanism, the contact surface region is operable to contact the face region of the user; and
the first fit adjustment mechanism is operable to control where at the contact surface region that the contact surface region contacts the face region of the user when the mask structure is coupled to the face region of the user by the attachment mechanism.

14. The respirator of claim 13 wherein:
when the mask structure is coupled to the face region of the user by the attachment mechanism, the contact surface region is operable to automatically conform to the face region of the user.

15. The respirator of claim 13 wherein:

when the mask structure is coupled to the face region of the user by the attachment mechanism, the contact surface region forms a mechanical seal around the face region of the user.

16. The respirator of claim 15 wherein:

the mechanical seal comprises a mechanical seal shape; and the mechanical seal shape comprises one of an egg curve shape or a pear curve shape.

17. The respirator of claim 13 wherein:

the multiple folds comprise plural folds configured such that at least part of the mask structure comprises a negative Poisson ratio.

18. The respirator of claim 13 wherein:

the multiple folds comprise at least one of:

first folds arranged in one or more waterbomb folding patterns;

second folds arranged in one or more Ron Resch folding patterns; or third folds arranged in one or more Miura-ori folding patterns.

19. The respirator of claim 13 wherein:

the mask structure is devoid of a malleable band operable to conform the contact surface region to the face region of the user.

20. The respirator of claim 13, wherein:

the multiple folds are arranged to cause at least part of the mask structure to behave auxetically.

* * * * *